(12) United States Patent
Federspiel et al.

(10) Patent No.: US 7,132,237 B2
(45) Date of Patent: Nov. 7, 2006

(54) AVIAN LEUKOSIS VIRUSES AND POLYPEPTIDE DISPLAY

(75) Inventors: Mark J. Federspiel, Rochester, MN (US); Stephen J. Russell, Rochester, MN (US); Pranay D. Khare, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 742 days.

(21) Appl. No.: 10/098,935

(22) Filed: Mar. 13, 2002

(65) Prior Publication Data

US 2004/0180326 A1  Sep. 16, 2004

(51) Int. Cl.
  *C12Q 1/70* (2006.01)
  *C12Q 1/68* (2006.01)
(52) U.S. Cl. .............................. 435/6; 435/5
(58) Field of Classification Search ............ 424/199.1, 424/201.1, 192.1, 204.1, 207.1; 514/44
  See application file for complete search history.

(56) References Cited

U.S. PATENT DOCUMENTS

| | | | |
|---|---|---|---|
| 4,683,195 A | 7/1987 | Mullis et al. | 435/6 |
| 5,723,287 A * | 3/1998 | Russell et al. | 435/5 |
| 6,096,534 A | 8/2000 | Barsov et al. | 435/320.1 |

OTHER PUBLICATIONS

Chebloune et al., "Immune Response and Resistance to Rous Sarcoma Virus Challenge of Chickens Immunized with Cell-Associated Glycoproteins Provided with a Recombinant Avian Leukosis Virus," Journal of Virology, vol. 65, No. 10, Oct. 1991, p. 5374-5380.*

Khare et al. "Replication Competent Avian Leukosis Virus: A Novel System for Stable Polypeptides Display," Gene Therapy, Abstracts for Harold W. Siebens Conference, Oct. 5-7, 2001, vol. 8, Supplement 1, Mayo Foundation, Rochester, Minnesota, p. s9.*

Khare et al., "Stable Display of Polypeptides on Avian Leukosis Virus Envelope Glycoproteins," Abstracts of papers presented at the 2001 meeting on Vector Targeting Strategies for Gene Therapy, Mar. 15-18, 2001, Cold Spring Harbor Laboratory, NY, p. 12.*

Arap et al., "Cancer Treatment by Targeted Drug Delivery to Tumor Vasculature in a Mouse Model," *Science*, 1998, 279:377-380.

Boerger et al., "Retroviral vectors preloaded with a viral receptor-ligand bridge protein are targeted to specific cell types," *Proc. Natl. Acad. Sci. USA*, 1999, 96:9867-9872.

Ellerby et al., "Anti-cancer activity of targeted pro-apoptotic peptides," *Nature Medicine*, 1999, 5(9):1032-1038.

(Continued)

*Primary Examiner*—Bruce R. Campell
*Assistant Examiner*—M. Franco Salvoza
(74) *Attorney, Agent, or Firm*—Fish & Richardson P.C.

(57) ABSTRACT

The invention provides methods and materials involved in displaying polypeptide sequences using viruses such as avian leukosis viruses. Specifically, the invention provides nucleic acid molecules, collections of nucleic acid molecules, polypeptides, collections of polypeptides, viruses, and collections of viruses as well as methods for making nucleic acid molecules, collections of nucleic acid molecules, polypeptides, collections of polypeptides, viruses, and collections of viruses. The invention also provides methods for obtaining displayed polypeptide sequences that interact with biological molecules and/or cells as well as methods for identifying biological molecules that interact with displayed polypeptides.

1 Claim, 8 Drawing Sheets

OTHER PUBLICATIONS

Federspiel and Hughes, "Retroviral Gene Delivery," *Methods in Cell Biology*, 1998, vol. 52, Chapter 9, Academic Press, pp. 179-214.

Ferber, "Gene Therapy: Safer and Virus Free?" *Science*, 2001, 294(5547:1638-1642.

Holmen and Federspiel, "Selection of a Subgroup A Avian Leukosis Virus [ALV(A)] Envelope Resistant to Soluble ALV(A) Surface Glycoprotein," *Virology*, 2000, 273:364-373.

Holmen et al., "Identification of Key Residues in Subgroup A Avian Leukosis Virus Envelope Determining Receptor Binding Affinity and Infectivity of Cells Expressing Chicken or Quail Tva Receptor," *J. Virol.*, 2001, 75(2):726-737.

Khare et al., "Stable Display of Polypeptides on Avian Leukosis Virus Envelop Glycoproteins," *Abstracts of papers presented at the 2001 meeting on Vector Targeting Strategies for Gene Therapy*, Mar. 15-18, 2001, Cold Spring Harbor Laboratory, Cold Spring Harbor, New York, p. 12.

Khare et al., "Replication Competent Avian Leukosis Virus: A Novel System for Stable Polypeptides Display," *Gene Therapy*, Abstracts for Harold W. Siebens Conference, Oct. 5-7, 2001, vol. 8, Supplement 1, Mayo Foundation, Rochester, Minnesota, p. S9.

Li, "Applications of display technology in protein analysis," *Nature Biotechnology*, 2000, 18(12):1251-1256.

Pasqualini and Ruoslahti, "Organ targeting *in vivo* using phage display peptide libraries," *Nature*, 1996, 380:364-366.

Pinto et al., "Restricting Expression Prolongs Expression of Foreign Genes Introduced into Animals by Retroviruses," *J. Virol.*, 2000, 74(21):10202-10206.

Rajotte et al., "Molecular Heterogeneity of the Vascular Endothelium Revealed by In Vivo Phage Display," *J. Clin. Invest.*, 1998, 102:430-437.

Rajotte and Ruoslahti, "Membrane Dipeptidase Is the Receptor for a Lung-targeting Peptide Identified by *in Vivo* Phage Display," *J. Biol. Chem.*, 1999, 274(17):11593-11598.

Smith and Petrenko, "Phage Display," *Chem. Rev.*, 1997, 97:391-410.

Snitkovsky et al., "A TVA-Single-Chain Antibody Fusion Protein Mediates Specific Targeting of a Subgroup A Avian Leukosis Virus Vector to Cells Expressing a Tumor-Specific Form of Epidermal Growth Factor Receptor," *J. Virol.*, 2000, 74(20):9540-9545.

Trepel et al., "Molecular Adaptors for Vascular-Targeted Adenoviral Gene Delivery," *Human Gene Therapy*, 2000, 11:1971-1981.

Valsesia-Wittmann et al., "Modifications in the Binding Domain of Avian Retrovirus Envelope Protein To Redirect the Host Range of Retroviral Vectors," *J. Virol.*, 1994, 68(7):4609-4619.

* cited by examiner

First Re-passage　　　　　Second Re-passage

Figure 8

Step 1. Construct randomized plasmid libraries of peptides on the N-terminus of the ALV envelope glycoprotein.

↓

Schematic representation of the RCASBP(A) retroviral vector

| Sfi I | | Not I | |
|---|---|---|---|
| AAQPA | $X_{10}$ | AAA | Random peptides |
| AAQPA | $X_2NXTX_7$ | AAA | N-linked glycosylation peptides |
| AAQPA | $CX_2NXSX_7C$ | AAA | Cyclic glycosylated peptides |

The amino acid sequence of displayed proposed peptide libraries.

↓

Step 2. Transfection of the plasmid DNA containing infectious molecular clones of the ALV vector/peptide library into DF-1 cells to produce virus library.

↓

Library of ALV viruses displaying the peptide library

SEQUENCE LISTING

```
<160> NUMBER OF SEQ ID NOS: 17

<210> SEQ ID NO 1
<211> LENGTH: 340
<212> TYPE: PRT
<213> ORGANISM: Avian leukosis virus

<400> SEQUENCE: 1
```

Asp Val His Leu Leu Glu Gln Pro Gly Asn Leu Trp Ile Thr Trp Ala
1               5                   10                  15

Asn Arg Thr Gly Gln Thr Asp Phe Cys Leu Ser Thr Gln Ser Ala Thr
            20                  25                  30

Ser Pro Phe Gln Thr Cys Leu Ile Gly Ile Pro Ser Pro Ile Ser Glu
        35                  40                  45

Gly Asp Phe Lys Gly Tyr Val Ser Asp Thr Asn Cys Thr Thr Leu Gly
    50                  55                  60

Thr Asp Arg Leu Val Ser Ser Ala Asp Phe Thr Gly Gly Pro Asp Asn
65                  70                  75                  80

Ser Thr Thr Leu Thr Tyr Arg Lys Val Ser Cys Leu Leu Leu Lys Leu
                85                  90                  95

Asn Val Ser Met Trp Asp Glu Pro Pro Glu Leu Gln Leu Leu Gly Ser

```
                100             105             110
Gln Ser Leu Pro Asn Ile Thr Asn Ile Ala Gln Ile Ser Gly Ile Thr
            115                 120                 125

Gly Gly Cys Val Gly Phe Arg Pro Gln Gly Val Pro Trp Tyr Leu Gly
        130                 135                 140

Trp Ser Arg Gln Glu Ala Thr Arg Phe Leu Arg His Pro Ser Phe
145                 150                 155                 160

Ser Lys Ser Thr Glu Pro Phe Thr Val Val Thr Ala Asp Arg His Asn
                165                 170                 175

Leu Phe Met Gly Ser Glu Tyr Cys Gly Ala Tyr Gly Tyr Arg Phe Trp
            180                 185                 190

Asn Met Tyr Asn Cys Ser Gln Val Gly Arg Gln Tyr Arg Cys Gly Asn
        195                 200                 205

Ala Arg Ser Pro Arg Pro Gly Leu Pro Glu Ile Gln Cys Thr Arg Arg
        210                 215                 220

Gly Gly Lys Trp Val Asn Gln Ser Gln Glu Ile Asn Glu Ser Glu Pro
225                 230                 235                 240

Phe Ser Phe Thr Val Asn Cys Thr Ala Ser Ser Leu Gly Asn Ala Ser
                245                 250                 255

Gly Cys Cys Gly Lys Ala Gly Thr Ile Leu Pro Gly Lys Trp Tyr Asp
            260                 265                 270

Ser Thr Gln Gly Ser Phe Thr Lys Pro Lys Ala Leu Pro Pro Ala Ile
        275                 280                 285

Phe Leu Ile Cys Gly Asp Arg Ala Trp Gln Gly Ile Pro Ser Arg Pro
        290                 295                 300

Val Gly Gly Pro Cys Tyr Leu Gly Lys Leu Thr Met Leu Ala Pro Lys
305                 310                 315                 320

His Thr Asp Ile Leu Lys Val Leu Val Asn Ser Ser Arg Thr Gly Ile
                325                 330                 335

Arg Arg Lys Arg
            340

<210> SEQ ID NO 2
<211> LENGTH: 346
<212> TYPE: PRT
<213> ORGANISM: Avian leukosis virus

<400> SEQUENCE: 2

Asp Val His Leu Leu Glu Gln Pro Gly Asn Leu Trp Ile Thr Trp Ala
 1               5                  10                  15

Asn Arg Thr Gly Gln Thr Asp Phe Cys Leu Ser Thr Gln Ser Ala Thr
            20                  25                  30

Ser Pro Phe Gln Thr Cys Leu Ile Gly Ile Pro Ser Pro Ile Ser Glu
        35                  40                  45

Gly Asp Phe Lys Gly Tyr Val Ser Asp Asn Cys Thr Thr Leu Glu Pro
    50                  55                  60

His Arg Leu Val Ser Arg Gly Ile Pro Gly Gly Pro Asp Asn Ser Thr
65                  70                  75                  80

Thr Leu Thr Tyr Gln Lys Val Ser Cys Leu Leu Lys Leu Asn Val
            85                  90                  95

Ser Leu Leu Asp Glu Pro Ser Glu Leu Gln Leu Gly Ser Gln Ser
                100                 105                 110

Leu Pro Asn Ile Thr Asn Ile Thr Arg Ile Pro Ser Val Ala Gly Gly
            115                 120                 125
```

```
Cys Ile Gly Phe Thr Pro Tyr Asp Ser Pro Ala Gly Val Tyr Gly Trp
130                 135                 140

Asp Arg Arg Glu Val Thr His Ile Leu Leu Thr Asp Pro Gly Asn Asn
145                 150                 155                 160

Pro Phe Phe Asp Lys Ala Ser Asn Ser Ser Lys Pro Phe Thr Val Val
                165                 170                 175

Thr Ala Asp Arg His Asn Leu Phe Met Gly Ser Glu Tyr Cys Gly Ala
                180                 185                 190

Tyr Gly Tyr Arg Phe Trp Glu Met Tyr Asn Cys Ser Gln Met Arg Gln
            195                 200                 205

Asn Trp Ser Ile Cys Gln Asp Val Trp Arg Gly Pro Pro Glu Asn
210                 215                 220

Trp Cys Thr Ser Thr Gly Gly Thr Trp Val Asn Gln Ser Lys Glu Phe
225                 230                 235                 240

Asn Glu Thr Ala Pro Phe Ser Phe Thr Val Asn Cys Thr Gly Ser Asn
                245                 250                 255

Leu Gly Asn Val Ser Gly Cys Cys Gly Glu Pro Ile Thr Ile Leu Pro
                260                 265                 270

Pro Glu Ala Trp Val Asp Ser Thr Gln Gly Ser Phe Thr Lys Pro Lys
            275                 280                 285

Ala Leu Pro Pro Ala Ile Phe Leu Ile Cys Gly Asp Arg Ala Trp Gln
290                 295                 300

Gly Ile Pro Ser Arg Pro Ile Gly Gly Pro Cys Tyr Leu Gly Lys Leu
305                 310                 315                 320

Thr Met Leu Ala Pro Asn His Thr Asp Ile Leu Lys Ile Leu Ala Asn
                325                 330                 335

Ser Ser Gln Thr Gly Ile Arg Arg Lys Arg
                340                 345

<210> SEQ ID NO 3
<211> LENGTH: 339
<212> TYPE: PRT
<213> ORGANISM: Avian leukosis virus

<400> SEQUENCE: 3

Asp Val His Leu Leu Glu Gln Pro Gly Asn Leu Trp Ile Thr Trp Ala
1               5                   10                  15

Asn Arg Thr Gly Gln Thr Asp Phe Cys Leu Ser Thr Gln Ser Ala Thr
                20                  25                  30

Ser Pro Phe Gln Thr Cys Leu Ile Gly Ile Pro Ser Pro Ile Ser Glu
            35                  40                  45

Gly Asp Phe Lys Gly Tyr Val Ser Asp Thr Asn Cys Ser Thr Val Gly
50                  55                  60

Thr Asp Arg Leu Val Leu Ser Ala Ser Ile Thr Gly Gly Pro Asp Asn
65                  70                  75                  80

Ser Thr Thr Leu Thr Tyr Arg Lys Val Ser Cys Leu Leu Leu Lys Leu
                85                  90                  95

Asn Val Ser Met Trp Asp Glu Pro Pro Glu Leu Gln Leu Leu Gly Ser
                100                 105                 110

Gln Ser Leu Pro Asn Val Thr Asn Ile Thr Gln Val Ser Gly Val Ala
            115                 120                 125

Gly Gly Cys Val Tyr Phe Ala Pro Arg Ala Thr Gly Leu Phe Leu Gly
130                 135                 140

Trp Ser Lys Gln Gly Leu Ser Arg Phe Leu Leu Arg His Pro Phe Thr
145                 150                 155                 160
```

```
Ser Thr Ser Asn Ser Thr Glu Pro Phe Thr Val Thr Ala Asp Arg
            165                 170                 175

His Asn Leu Phe Met Gly Ser Glu Tyr Cys Gly Ala Tyr Gly Tyr Arg
            180                 185                 190

Phe Trp Glu Ile Tyr Asn Cys Ser Gln Thr Arg Asn Thr Tyr Arg Cys
            195                 200                 205

Gly Asp Val Gly Gly Thr Gly Leu Pro Glu Thr Trp Cys Arg Gly Lys
            210                 215                 220

Gly Gly Ile Trp Val Asn Gln Ser Lys Glu Ile Asn Glu Thr Glu Pro
225                 230                 235                 240

Phe Ser Phe Thr Ala Asn Cys Thr Gly Ser Asn Leu Gly Asn Val Ser
                245                 250                 255

Gly Cys Cys Gly Glu Pro Ile Thr Ile Leu Pro Leu Gly Ala Trp Ile
                260                 265                 270

Asp Ser Thr Gln Gly Ser Phe Thr Lys Pro Lys Ala Leu Pro Pro Ala
                275                 280                 285

Ile Phe Leu Ile Cys Gly Asp Arg Ala Trp Gln Gly Ile Pro Ser Arg
            290                 295                 300

Pro Val Gly Gly Pro Cys Tyr Leu Gly Lys Leu Thr Met Leu Ala Pro
305                 310                 315                 320

Asn His Thr Asp Ile Leu Lys Ile Leu Ala Asn Ser Ser Arg Thr Gly
                325                 330                 335

Ile Arg Arg

<210> SEQ ID NO 4
<211> LENGTH: 346
<212> TYPE: PRT
<213> ORGANISM: Avian leukosis virus

<400> SEQUENCE: 4

Asp Val His Leu Leu Glu Gln Pro Gly Asn Leu Trp Ile Thr Trp Ala
1               5                   10                  15

```
Ala Tyr Gly Tyr Arg Phe Trp Glu Met Tyr Asn Cys Ser Gln Ile Arg
            195                 200                 205

Asn Tyr Ser Ile Cys Glu Asp Val Trp Gly Gly Leu Pro Glu Ser
            210                 215                 220

Trp Cys Ala Arg Thr Gly Thr Trp Val Asn Lys Ser Lys Glu Ile
225                 230                 235                 240

Asn Glu Thr Glu Pro Ile Ser Phe Thr Val Asn Cys Thr Gly Ser Asn
                    245                 250                 255

Leu Gly Asn Val Ser Gly Cys Cys Gly Glu Ala Ile Thr Ile Leu Pro
            260                 265                 270

Leu Gly Ala Trp Val Asp Ser Thr Gln Gly Ser Phe Thr Lys Pro Lys
            275                 280                 285

Ala Leu Pro Pro Gly Ile Phe Leu Ile Cys Gly Asp Arg Ala Trp Gln
            290                 295                 300

Gly Thr Pro Ser Arg Pro Val Gly Gly Pro Cys Tyr Leu Gly Lys Leu
305                 310                 315                 320

Thr Met Leu Ala Pro Asn His Thr Asn Ile Leu Lys Ile Leu Ala Asn
                    325                 330                 335

Ser Ser Arg Thr Gly Ile Arg Arg Lys Arg
            340                 345

<210> SEQ ID NO 5
<211> LENGTH: 350
<212> TYPE: PRT
<213> ORGANISM: Avian leukosis virus

<400> SEQUENCE: 5

Asp Val His Leu Leu Glu Gln Pro Gly Asn Leu Trp Ile Thr Trp Ala
1               5                   10                  15

Asn Arg Thr Gly Gln Thr Asp Phe Cys Leu Ser Thr Gln Ser Ala Thr
            20                  25                  30

Ser Pro Phe Gln Thr Cys Leu Ile Gly Ile Pro Ser Pro Ile Ser Glu
        35                  40                  45

Gly Asp Phe Lys Gly Tyr Val Ser Asp Thr Asn Cys Thr Thr Leu Gly
50                  55                  60

Thr Asp Arg Leu Val Ser Ser Ala Ser Ile Thr Gly Gly Pro Asp Asn
65                  70                  75                  80

Ser Thr Thr Leu Thr Tyr Arg Lys Val Ser Cys Leu Leu Leu Lys Leu
                    85                  90                  95

Asn Val Ser Met Trp Asp Glu Pro Pro Glu Leu Gln Leu Leu Gly Ser
            100                 105                 110

Gln Ser Leu Pro Asn Ile Thr Asn Ile Thr Gln Ile Ser Gly Val Thr
            115                 120                 125

Gly Gly Cys Val Gly Phe Ala Pro His Ser Asn Pro Ser Gly Val Tyr
130                 135                 140

Gly Trp Gly Arg Arg Gln Val Thr His Asn Phe Leu Ile Ala Pro Trp
145                 150                 155                 160

Val Asn Pro Phe Phe Asn Ser Ala Ser Asn Ser Thr Glu Pro Phe Thr
                165                 170                 175

Val Val Thr Ala Asp Arg His Asn Leu Phe Met Gly Ser Glu Tyr Cys
            180                 185                 190

Gly Ala Tyr Gly Tyr Arg Phe Trp Glu Ile Tyr Asn Cys Ser His Arg
            195                 200                 205

Phe Asp Asn Phe Asp Ile Tyr Thr Cys Gly Asp Val Gln Thr Val Lys
```

-continued

```
                210                 215                 220
Ser Pro Glu Lys Gln Cys Val Gly Gly Gly Ile Trp Val Asn Gln
225                 230                 235                 240

Ser Lys Glu Ile Asn Glu Thr Glu Pro Phe Ser Phe Thr Ala Asn Cys
                245                 250                 255

Thr Ala Ser Asn Leu Gly Asn Val Ser Gly Cys Cys Gly Lys Thr Ile
                260                 265                 270

Thr Ile Leu Pro Ser Gly Ala Trp Val Asp Ser Thr Gln Gly Ser Phe
            275                 280                 285

Thr Lys Pro Lys Ala Leu Pro Pro Ala Ile Phe Leu Ile Cys Gly Asp
    290                 295                 300

Arg Ala Trp Gln Gly Ile Pro Ser Arg Pro Val Gly Gly Pro Cys Tyr
305                 310                 315                 320

Leu Gly Lys Leu Thr Met Leu Ala Pro Asn His Thr Asp Ile Leu Lys
                325                 330                 335

Ile Leu Ala Asn Ser Ser Arg Thr Gly Ile Arg Arg Lys Arg
                340                 345                 350

<210> SEQ ID NO 6
<211> LENGTH: 352
<212> TYPE: PRT
<213> ORGANISM: Artificial Sequence
<220> FEATURE:
<223> OTHER INFORMATION: Consensus sequence
<220> FEATURE:
<221> NAME/KEY: Variant
<222> LOCATION: 135
<223> OTHER INFORMATION: Xaa = Arg, Ala, or Thr
<220> FEATURE:
<221> NAME/KEY: Variant
<222> LOCATION: 137
<223> OTHER INFORMATION: Xaa = Gln, Tyr, Arg, or His
<220> FEATURE:
<221> NAME/KEY: Variant
<222> LOCATION: 138
<223> OTHER INFORMATION: Xaa = Gly, Asp, Ala, or Ser
<220> FEATURE:
<221> NAME/KEY: Variant
<222> LOCATION: 139
<223> OTHER INFORMATION: Xaa = Val, Ser, Thr, or Asn
<220> FEATURE:
<221> NAME/KEY: Variant
<222> LOCATION: 147
<223> OTHER INFORMATION: Xaa = Ser, Asp, or Gly
<220> FEATURE:
<221> NAME/KEY: Variant
<222> LOCATION: 149
<223> OTHER INFORMATION: Xaa = Gln, Arg, or Glu
<220> FEATURE:
<221> NAME/KEY: Variant
<222> LOCATION: 154
<223> OTHER INFORMATION: Xaa = Phe, Ile, or Asn
<220> FEATURE:
<221> NAME/KEY: Variant
<222> LOCATION: 157
<223> OTHER INFORMATION: Xaa = Arg, Thr, or Ile
<220> FEATURE:
<221> NAME/KEY: Variant
<222> LOCATION: 158
<223> OTHER INFORMATION: Xaa = His, Asp, Asn, or Ala
<220> FEATURE:
<221> NAME/KEY: Variant
<222> LOCATION: 160
<223> OTHER INFORMATION: Xaa = Gly, Phe, Pro, or Trp
<220> FEATURE:
<221> NAME/KEY: Variant
<222> LOCATION: 161
<223> OTHER INFORMATION: Xaa = Asn, Thr, Asp, or Val
<220> FEATURE:
<221> NAME/KEY: Variant
```

```
<222> LOCATION: 208
<223> OTHER INFORMATION: Xaa = Val, Met, Thr, Ile, or Arg
<220> FEATURE:
<221> NAME/KEY: Variant
<222> LOCATION: 210
<223> OTHER INFORMATION: Xaa = Arg, Gln, Asn, or Asp
<220> FEATURE:
<221> NAME/KEY: Variant
<222> LOCATION: 214
<223> OTHER INFORMATION: Xaa = Gln, Trp, Thr, Tyr, or Ile
<220> FEATURE:
<221> NAME/KEY: Variant
<222> LOCATION: 216
<223> OTHER INFORMATION: Xaa = Arg, Ile, or Thr
<220> FEATURE:
<221> NAME/KEY: Variant
<222> LOCATION: 221
<223> OTHER INFORMATION: Xaa = Arg, Trp, Gly, or Gln
<220> FEATURE:
<221> NAME/KEY: Variant
<222> LOCATION: 225
<223> OTHER INFORMATION: Xaa = Pro, Arg, Thr, or Val
<220> FEATURE:
<221> NAME/KEY: Variant
<222> LOCATION: 230
<223> OTHER INFORMATION: Xaa = Ile, Asn, Thr, Ser, or Lys
<220> FEATURE:
<221> NAME/KEY: Variant
<222> LOCATION: 233
<223> OTHER INFORMATION: Xaa = Thr, Arg, Ala, or Val
<220> FEATURE:
<221> NAME/KEY: Variant
<222> LOCATION: 234
<223> OTHER INFORMATION: Xaa = Arg, Ser, or Gly
<220> FEATURE:
<221> NAME/KEY: Variant
<222> LOCATION: 235
<223> OTHER INFORMATION: Xaa = Arg, Thr, Lys, or Gly
<220> FEATURE:
<221> NAME/KEY: Variant
<222> LOCATION: 238
<223> OTHER INFORMATION: Xaa = Lys, Thr, or Ile
<220> FEATURE:
<221> NAME/KEY: Variant
<222> LOCATION: 273
<223> OTHER INFORMATION: Xaa = Ala, Pro, or Thr
<220> FEATURE:
<221> NAME/KEY: Variant
<222> LOCATION: 279
<223> OTHER INFORMATION: Xaa = Pro, Leu, or Ser

<400> SEQUENCE: 6

Asp Val His Leu Leu Glu Gln Pro Gly Asn Leu Trp Ile Thr Trp Ala
 1               5                  10                  15

Asn Arg Thr Gly Gln Thr Asp Phe Cys Leu Ser Thr Gln Ser Ala Thr
            20                  25                  30

Ser Pro Phe Gln Thr Cys Leu Ile Gly Ile Pro Ser Pro Ile Ser Glu
        35                  40                  45

Gly Asp Phe Lys Gly Tyr Val Ser Asp Thr Asn Cys Thr Thr Leu Gly
 50                  55                  60

Thr Asp Arg Leu Val Ser Ser Ala Ser Ile Thr Gly Gly Pro Asp Asn
65                  70                  75                  80

Ser Thr Thr Leu Thr Tyr Arg Lys Val Ser Cys Leu Leu Lys Leu
            85                  90                  95

Asn Val Ser Met Trp Asp Glu Pro Pro Glu Leu Gln Leu Leu Gly Ser
            100                 105                 110

Gln Ser Leu Pro Asn Ile Thr Asn Ile Thr Gln Ile Ser Gly Val Ala
        115                 120                 125

Gly Gly Cys Val Gly Phe Xaa Pro Xaa Xaa Xaa Pro Ala Gly Val Tyr
130                 135                 140
```

```
Gly Trp Xaa Arg Xaa Glu Val Thr His Xaa Leu Leu Xaa Xaa Pro Xaa
145                 150                 155                 160

Xaa Asn Pro Phe Phe Asn Ser Ala Ser Asn Ser Thr Glu Pro Phe Thr
                165                 170                 175

Val Val Thr Ala Asp Arg His Asn Leu Phe Met Gly Ser Glu Tyr Cys
            180                 185                 190

Gly Ala Tyr Gly Tyr Arg Phe Trp Glu Met Tyr Asn Cys Ser Gln Xaa
        195                 200                 205

Arg Xaa Asn Phe Asp Xaa Tyr Xaa Cys Gly Asp Val Xaa Gly Pro Arg
    210                 215                 220

Xaa Gly Leu Pro Glu Xaa Trp Cys Xaa Xaa Xaa Gly Gly Xaa Trp Val
225                 230                 235                 240

Asn Gln Ser Lys Glu Ile Asn Glu Thr Glu Pro Phe Ser Phe Thr Val
                245                 250                 255

Asn Cys Thr Gly Ser Asn Leu Gly Asn Val Ser Gly Cys Cys Gly Glu
            260                 265                 270

Xaa Ile Thr Ile Leu Pro Xaa Gly Ala Trp Val Asp Ser Thr Gln Gly
        275                 280                 285

Ser Phe Thr Lys Pro Lys Ala Leu Pro Pro Ala Ile Phe Leu Ile Cys
290                 295                 300

Gly Asp Arg Ala Trp Gln Gly Ile Pro Ser Arg Pro Val Gly Gly Pro
305                 310                 315                 320

Cys Tyr Leu Gly Lys Leu Thr Met Leu Ala Pro Asn His Thr Asp Ile
                325                 330                 335

Leu Lys Val Leu Ala Asn Ser Ser Arg Thr Gly Ile Arg Arg Lys Arg
            340                 345                 350

<210> SEQ ID NO 7
<211> LENGTH: 8
<212> TYPE: PRT
<213> ORGANISM: Artificial Sequence
<220> FEATURE:
<223> OTHER INFORMATION: Synthetically generated epitope

<400> SEQUENCE: 7

Asp Tyr Lys Asp Asp Asp Asp Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Restriction site peptide

<400> SEQUENCE: 8

Ala Ala Gln Pro Ala
1               5

<210> SEQ ID NO 9
<211> LENGTH: 4
<212> TYPE: PRT
<213> ORGANISM: Artificial Sequence
<220> FEATURE:
<223> OTHER INFORMATION: Cleavage site

<400> SEQUENCE: 9

Ile Glu Gly Arg
1
```

-continued

```
<210> SEQ ID NO 10
<211> LENGTH: 5
<212> TYPE: PRT
<213> ORGANISM: Artificial Sequence
<220> FEATURE:
<223> OTHER INFORMATION: Linker peptide

<400> SEQUENCE: 10

Gly Gly Gly Gly Ser
1               5

<210> SEQ ID NO 11
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2-3, 5, 7-13
<223> OTHER INFORMATION: Xaa = Any amino acid

<400> SEQUENCE: 11

Cys Xaa Xaa Asn Xaa Thr Xaa Xaa Xaa Xaa Xaa Xaa Xaa Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2-3, 5, 7-13
<223> OTHER INFORMATION: Xaa = Any amino acid

<400> SEQUENCE: 12

Cys Xaa Xaa Asn Xaa Ser Xaa Xaa Xaa Xaa Xaa Xaa Xaa Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Partial sequence from ALV envelope protein

<400> SEQUENCE: 13

Met Glu Ala Val Ile Lys Gln Ala Phe Leu Thr Gly
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Partial sequence from ALV envelope protein

<400> SEQUENCE: 14

Thr Gly Val Arg Ala Asp Val His Leu Leu Glu Gln Pro Gly Asn Leu
1               5                   10                  15

Trp

<210> SEQ ID NO 15
<211> LENGTH: 10
<212> TYPE: PRT
```

```
-continued

<213> ORGANISM: Artificial Sequence
<220> FEATURE:
<223> OTHER INFORMATION: Partial sequence from ALV envelope protein

<400> SEQUENCE: 15

Ala Cys Gly Gln Pro Glu Ser Arg Ile Val
 1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1-2, 4, 6-12
<223> OTHER INFORMATION: Xaa = Any amino acid

<400> SEQUENCE: 16

Xaa Xaa Asn Xaa Thr Xaa Xaa Xaa Xaa Xaa Xaa Xaa
 1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1-2, 4, 6-12
<223> OTHER INFORMATION: Xaa = Any amino acid

<400> SEQUENCE: 17

Xaa Xaa Asn Xaa Ser Xaa Xaa Xaa Xaa Xaa Xaa Xaa
 1               5                   10
```

AVIAN LEUKOSIS VIRUSES AND POLYPEPTIDE DISPLAY

BACKGROUND

1. Technical Field

The invention relates to methods and materials involved in displaying polypeptide sequences using viruses such as avian leukosis viruses.

2. Background Information

Display technology involves generating libraries of modularly coded biomolecules and screening those biomolecules for particular properties. One feature of display technology is to link a particular phenotype (e.g., a displayed polypeptide) to its genotype (e.g., a nucleic acid encoding the displayed polypeptide) so that the genotypes of selected phenotypes can be rapidly identified. Polypeptide display systems include viral display systems as well as cell-based display systems. Viral and cell-based display systems have the ability to amplify the selected population of displayed polypeptides.

Phage display has been used extensively as a platform for polypeptide display, accommodating a wide-range of polypeptides from small polypeptides to single chain antibodies. For example, phage display libraries have been used to select polypeptides that specifically bind to unique antigens on immobilized polypeptides and to targeted receptors on cultured cells (Li, M., *Nat. Biotech.*, 18:1251–1256 (2000)). In addition, in vivo selection strategies of phage display polypeptide libraries in mice have been developed (Pasqualini and Ruoslahti, *Nature*, 380:364–366 (1996)). These selection strategies allow cells, organs, and tumors to be studied in their natural environments, a complexity that is difficult to model in vitro. Thus, the power of polypeptide display technology for identifying new therapeutic targets such as targets for cancer treatment both in vitro and in vivo is clear.

SUMMARY

The invention provides methods and materials involved in displaying polypeptide sequences using viruses such as avian leukosis viruses (ALV). Specifically, the invention provides nucleic acid molecules, collections of nucleic acid molecules, polypeptides, collections of polypeptides, viruses, and collections of viruses. The invention also provides methods for making nucleic acid molecules, collections of nucleic acid molecules, polypeptides, collections of polypeptides, viruses, and collections of viruses.

The nucleic acid molecules and collections of nucleic acid molecules provided herein can encode ALV surface glycoproteins having N-terminal polypeptide extensions. Such nucleic acid molecules and collections of nucleic acid molecules can be used to produce ALV surface glycoproteins having N-terminal polypeptide extensions as well as viruses containing (1) ALV surface glycoproteins having N-terminal polypeptide extensions and/or (2) nucleic acid molecules encoding ALV surface glycoproteins having N-terminal polypeptide extensions. As described herein, viruses (e.g., ALV) containing ALV surface glycoproteins having N-terminal polypeptide extensions can be used as a polypeptide display platform, providing researchers with a powerful tool for, inter alia, identifying new therapeutic targets such as targets for cancer treatment.

In addition, the invention provides methods for obtaining displayed polypeptide sequences that interact with biological molecules (e.g., cell receptors and cell glycoproteins) and/or cells (e.g., cancer cells). For example, the methods and materials provided herein can be used to obtain displayed polypeptides that bind cell surface receptors, that mimic the properties of other polypeptides, or that bind specific cells or tissue surfaces. Likewise, the methods and materials provided herein can be used to identify optimal binding substrates and to elucidate polypeptide interactions such as polypeptide-polypeptide interactions and polypeptide-carbohydrate interactions. Such methods can help researchers develop new reagents to treat conditions such as cancer, autoimmunity, infections (e.g., viral infections, bacterial infections, and fungal infections), and central nervous system disorders (e.g., Parkinson's disease, Huntington's Disease, and Alzheimer's disease).

The invention provides methods for identifying biological molecules (e.g., cell receptors and cell glycoproteins) that interact with displayed polypeptides. Identifying biological molecules such as cell receptors primarily expressed by tumor cells can help researchers develop new reagents that specifically target those identified biological molecules. For example, identifying a cell surface receptor that is only expressed by breast tumor cells can help researchers develop drugs that target and destroy only breast tumor cells.

The invention is based on the discovery that ALV surface glycoproteins having N-terminal polypeptide extensions of various lengths can be efficiently incorporated into infectious virions. The invention also is based on the discovery that viruses containing ALV surface glycoproteins having N-terminal polypeptide extensions of various lengths can replicate efficiently, reaching infectious titers comparable to wild-type viruses. In addition, the invention is based on the discovery that viruses containing ALV surface glycoproteins having N-terminal polypeptide extensions of various lengths can (1) stably retain the N-terminal polypeptide extensions after repeated virus repassage and (2) bind both specific immobilized ligands as well as cells expressing specific ligands.

In one aspect, the invention features a nucleic acid molecule containing a first nucleic acid sequence, where the first nucleic acid sequence encodes a first polypeptide containing an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The first amino acid sequence can be between five and 500 amino acid residues in length, between ten and 250 amino acid residues in length, or between 15 and 100 amino acid residues in length. The first amino acid sequence can contain a sequence from a receptor, receptor ligand, immunoglobulin, enzyme, or enzyme substrate. The avian leukosis virus surface glycoprotein amino acid sequence can contain a sequence as set forth in SEQ ID NO: 1, 2, 3, 4, 5, or 6. The nucleic acid molecule can encode an avian leukosis virus transmembrane glycoprotein amino acid sequence. The first polypeptide can form a covalent attachment with an avian leukosis virus transmembrane glycoprotein when the first polypeptide is part of an avian leukosis virus. The nucleic acid molecule can contain a second nucleic acid sequence. The second nucleic acid sequence can be heterologous to naturally occurring avian leukosis virus sequences. The second nucleic acid sequence can encode a second polypeptide. The second polypeptide can be between five and 500 amino acid residues in length, between ten and 250 amino acid residues in length, or between 15 and 100 amino acid residues in length. The second polypeptide can be a receptor, receptor ligand, immunoglobulin, enzyme, or enzyme substrate. The nucleic acid molecule can contain a retroviral 5'-LTR sequence, a retroviral gag sequence, a retroviral pol sequence, and a retroviral 3'-LTR sequence. The second nucleic acid sequence can be located between the first nucleic acid sequence and the retroviral 3'-LTR sequence. The retroviral 5'-LTR sequence, the retroviral gag sequence, the retroviral pol sequence, and the retroviral 3'-LTR sequence can be avian leukosis virus sequences. The nucleic acid molecule can encode a replication-competent avian leukosis virus or a replication-defective avian leukosis virus.

In another embodiment, the invention features a plurality of nucleic acid molecules, where each nucleic acid molecule encodes a first polypeptide containing an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The avian leukosis virus surface glycoprotein amino acid sequence of each first polypeptide can be identical. The first amino acid sequence of each first polypeptide can be different. Each of the plurality of nucleic acid molecules can encode an avian leukosis virus transmembrane glycoprotein amino acid sequence. Each first polypeptide can form a covalent attachment with an avian leukosis virus transmembrane glycoprotein when each first polypeptide is part of an avian leukosis virus. Each of the plurality of nucleic acid molecules can contain a second nucleic acid sequence that encodes a second polypeptide.

Another aspect of the invention features a polypeptide containing an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The first amino acid sequence can be between five and 500 amino acid residues in length, between ten and 250 amino acid residues in length, or between 15 and 100 amino acid residues in length. The first amino acid sequence can contain a sequence from a receptor, receptor ligand, immunoglobulin, enzyme, or enzyme substrate. The avian leukosis virus surface glycoprotein amino acid sequence can contain a sequence as set forth in SEQ ID NO: 1, 2, 3, 4, 5, or 6. The polypeptide can form a covalent attachment with an avian leukosis virus transmembrane glycoprotein when the polypeptide is part of an avian leukosis virus.

In another embodiment, the invention features a plurality of polypeptides, where each polypeptide contains an avian leukosis virus surface glycoprotein amino acid sequence and a first amino acid sequence, where the first amino acid sequence of each polypeptide is heterologous to naturally occurring avian leukosis virus amino acid sequences, and where the first amino acid sequence of each polypeptide is attached to the amino-terminal portion of the avian leukosis virus surface glycoprotein amino acid sequence. The avian leukosis virus amino acid sequence of each polypeptide can be identical. The first amino acid sequence of each polypeptide can be different. Each polypeptide can form a covalent attachment with an avian leukosis virus transmembrane glycoprotein when part of an avian leukosis virus.

Another aspect of the invention features a virus containing a nucleic acid molecule containing a first nucleic acid sequence, where the first nucleic acid sequence encodes a first polypeptide containing an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The virus can be a retrovirus (e.g., an avian leukosis virus or a murine leukemia virus). The virus can contain the first polypeptide. The nucleic acid molecule can encode an avian leukosis virus transmembrane glycoprotein amino acid sequence. The first polypeptide can form a covalent attachment with an avian leukosis virus transmembrane glycoprotein when the first polypeptide is part of an avian leukosis virus. The virus can contain an avian leukosis virus transmembrane glycoprotein, and the first polypeptide can form a covalent attachment with the avian leukosis virus transmembrane glycoprotein. The nucleic acid molecule can contain a second nucleic acid sequence, the second nucleic acid sequence being heterologous to naturally occurring avian leukosis viruses. The second nucleic acid sequence can encode a second polypeptide. The virus can contain the second polypeptide. The second polypeptide can be a receptor, receptor ligand, immunoglobulin, enzyme, or enzyme substrate. The second nucleic acid sequence can be located between an env viral sequence and a 3' LTR viral sequence. The virus can be replication-competent or replication-defective.

In another embodiment, the invention features a virus containing a first polypeptide, where the first polypeptide contains an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The virus can be a retrovirus (e.g., an avian leukosis virus or a murine leukemia virus). The first polypeptide can form a covalent attachment with an avian leukosis virus transmembrane glycoprotein when the first polypeptide is part of an avian leukosis virus. The virus can contain an avian leukosis virus transmembrane glycoprotein, and the first polypeptide can form a covalent attachment with the avian leukosis virus transmembrane glycoprotein. The virus can contain a nucleic acid molecule containing a first nucleic acid sequence, where the first nucleic acid sequence encodes the first polypeptide. The nucleic acid molecule can contain a second nucleic acid sequence, where the second nucleic acid sequence is heterologous to naturally occurring avian leukosis viruses. The second nucleic acid sequence can encode a second polypeptide. The second polypeptide can be a receptor, receptor ligand, immunoglobulin, enzyme, or enzyme substrate. The second nucleic acid sequence can be located between the first nucleic acid sequence and a 3' LTR viral sequence. The virus can be replication-competent or replication-defective.

Another embodiment of the invention features a plurality of viruses, where each virus contains a nucleic acid molecule containing a first nucleic acid sequence, where the first nucleic acid sequence encodes a first polypeptide, where each first polypeptide contains an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The avian leukosis virus surface glycoprotein amino acid sequence of each first polypeptide can be identical. The first amino acid sequence of each first polypeptide can be different. Each virus can contain the first polypeptide. The nucleic acid molecule of each virus can contain a second nucleic acid sequence. The second nucleic acid sequence of each virus can be different. The second nucleic acid sequence can encode a second polypeptide. Each virus can contain the second polypeptide. Each virus can be replication-competent or replication-defective. The plurality can be at least 500.

Another embodiment of the invention features a plurality of viruses, where each virus contains a first polypeptide, where each first polypeptide contains an avian leukosis virus surface glycoprotein amino acid sequence and a first amino acid sequence, where the first amino acid sequence is heterologous to naturally occurring avian leukosis virus amino acid sequences, and where the first amino acid sequence is attached to the amino-terminal portion of the avian leukosis virus surface glycoprotein amino acid sequence. The avian leukosis virus surface glycoprotein amino acid sequence of each first polypeptide can be identical. The first amino acid sequence of each first polypeptide can be different. Each virus can contain a nucleic acid molecule containing a first nucleic acid sequence, where the first nucleic acid sequence encodes the first polypeptide. The nucleic acid molecule of each virus can contain a second nucleic acid sequence. The second nucleic acid sequence of each virus can be different. The second nucleic acid sequence can encode a second polypeptide. Each virus can contain the second polypeptide. Each virus can be replication-competent or replication-defective. The plurality can be at least 500.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 8 is a schematic representation of the steps that can be used to make an ALV polypeptide display library. The SD represents a splice donor, while the SA represents a splice acceptor.

DETAILED DESCRIPTION

The invention provides methods and materials related to the display of polypeptide sequences using viruses such as ALV. Specifically, the invention provides nucleic acid molecules, collections of nucleic acid molecules, polypeptides, collections of polypeptides, viruses, and collections of viruses as well as methods for making nucleic acid molecules, collections of nucleic acid molecules, polypeptides, collections of polypeptides, viruses, and collections of viruses. The invention also provides methods for obtaining displayed polypeptide sequences that interact with biological molecules (e.g., cell receptors and cell glycoproteins) and/or cells (e.g., cancer cells) as well as methods for identifying biological molecules (e.g., cell receptors and cell glycoproteins) that interact with displayed polypeptides.

1. Nucleic Acid

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

Figure 10:
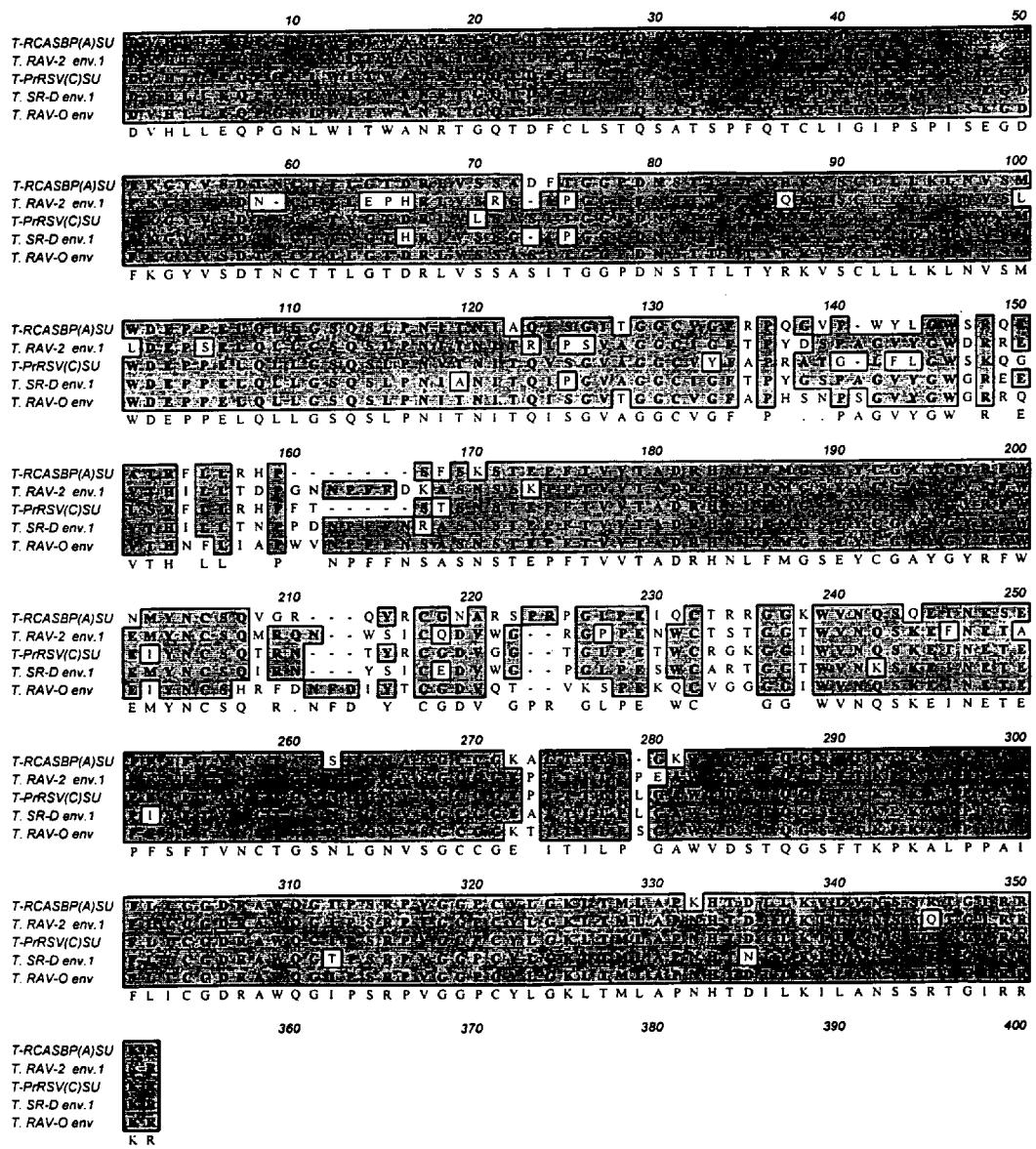
FIG. 10 is a sequence alignment of five ALV surface glycoprotein amino acid sequences. The first sequence designated T-RCASBP(A)SU represents SEQ ID NO:1; the second sequence designated T.RAV-2 env.1 represents SEQ ID NO:2; the third sequence designated T.PrRSV(C)SU represents SEQ ID NO:3; the fourth sequence designated T.SR-D env.1 represents SEQ ID NO:4; and the fifth sequence designated T.RAV-O env represents SEQ ID NO:5. The sixth sequence listed under the first five sequences represents a consensus sequence with each blank space or dot (.) being any one of the amino acid residues aligned directly above that particular space or dot. For example, the space at position 238 of the consensus sequence can be a lysine, threonine, or isoleucine. This consensus sequence represents SEQ ID NO:6.

The invention provides nucleic acid molecules that encode polypeptides having (1) an ALV surface glycoprotein amino acid sequence and (2) an amino acid sequence heterologous to any naturally occurring ALV amino acid sequence. Typically, the heterologous amino acid sequence is attached to the amino-terminal portion of the ALV surface glycoprotein amino acid sequence. For example, the nucleic acid molecules of the invention can encode polypeptides where each polypeptide has a different amino acid sequence (e.g., a different non-ALV sequence) attached to the amino-terminal portion of an ALV surface glycoprotein amino acid sequence. The term "ALV surface glycoprotein amino acid sequence" as used herein refers to any amino acid sequence that is at least 65 percent (e.g., at least 70, 75, 80, 85, 90, 95, 99, or 100 percent) identical to an ALV surface glycoprotein amino acid sequence as found in nature. In addition, an ALV surface glycoprotein amino acid sequence can form a covalent attachment with an ALV transmembrane glycoprotein when they are expressed by a cell or incorporated into a virus. Such ALV surface glycoprotein amino acid sequences include, without limitation, the amino acid sequences set forth in FIG. 10.

The percent identity between a particular amino acid sequence and an ALV surface glycoprotein amino acid sequence found in nature is determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., "www" dot "fr" dot "com" slash "blast" slash) or the U.S. government's National Center for Biotechnology Information web site ("www" dot "ncbi" dot "nlm" dot "nih" dot "gov"). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical amino acid residue is presented in both sequences. The percent identity is determined by dividing the number of matches by the length of the full-length ALV surface glycoprotein amino acid sequence followed by multiplying the resulting value by 100. For example, an amino acid sequence that has 273 matches when aligned with the sequence set forth in SEQ ID NO:1 is 80.1 percent identical to the sequence set forth in SEQ ID NO:1 (i.e., 273÷341*100=80.1).

It is noted that the percent identity value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

Again, the nucleic acid molecules provided herein encode polypeptides having a heterologous amino acid sequence attached to the amino-terminal portion of an ALV surface glycoprotein amino acid sequence. The amino-terminal portion of an amino acid sequence refers to any part of that amino acid sequence that is within at least the first 25 amino-terminal amino acid residues (e.g., within at least the first 20, 15, 10, 5, or less amino-terminal amino acid residues) of that amino acid sequence. For example, a polypeptide having a 100-amino acid non-viral sequence inserted between the fifth and sixth amino acid residues of the amino acid sequence set forth in SEQ ID NO:1 is a polypeptide having an ALV surface glycoprotein amino acid sequence with a heterologous amino-terminal extension. It is noted that the heterologous amino acid sequences described herein can be attached to an ALV surface glycoprotein amino acid sequence via a region other than an amino-terminal portion. For example, a heterologous amino acid sequence can be attached to the first, second, third, or fourth 50 amino acid segment of an ALV surface glycoprotein amino acid sequence.

The nucleic acid sequence that encodes the amino acid sequence attached to the amino-terminal portion of an ALV surface glycoprotein amino acid sequence can encode any amino acid sequence heterologous to any naturally occurring ALV amino acid sequence. Such nucleic acid sequences include, without limitation, sequences that encode epitopes (e.g., the FLAG® epitope), ligands (e.g., the EGF ligand), protease cleavage sites (e.g., a Factor Xa cleavage site), linkers (e.g., a G4S linker), and/or randomized amino acid sequences of any length. In addition, such nucleic acid sequences can encode linear polypeptides or cyclic polypeptides. For example, a randomized nucleic acid sequence can be flanked by cysteine residues such that the cysteine residues form a cyclic structure via a covalent linkage. Further, such nucleic acid sequences can encode an amino acid motif (e.g., an N-linked glycosylation signal) that is modified via glycosylation. For example, a nucleic acid sequence can encode NXT or NXS; where N represents an asparagine residue, X represents any amino acid residue, T represents a threonine residue, and S represents a serine residue. The length of the heterologous amino acid sequence attached to the amino-terminal portion of an ALV surface glycoprotein amino acid sequence can be greater than 5 (e.g., greater than 6, 7, 8, 9, 10, 11, 12, 13, 14, 15, 20, 25, 35, 50, 75, 100, 250, 500, or 1000) amino acid residues. For example, the heterologous amino acid sequence attached to the amino-terminal portion of an ALV surface glycoprotein amino acid sequence can be between 5 and 5000 amino acid residues in length (e.g., between 5 and 1000, 5 and 500, 10 and 500, 10 and 250, or 10 and 100 amino acid residues in length). In one embodiment, a nucleic acid molecule within the scope of the invention contains, in the 5' to 3' direction, a first restriction enzyme cleavage site, a sequence that encodes 10 to 50 amino acid residues, a second restriction enzyme cleavage site, a sequence that encodes a G4S linker, and a sequence that encodes an ALV surface glycoprotein.

The nucleic acid molecules provided herein can contain additional nucleic acid sequences. For example, a nucleic acid molecule can contain a nucleic acid sequence that encodes an ALV transmembrane glycoprotein amino acid sequence. Typically, the nucleic acid sequence encoding an ALV transmembrane glycoprotein amino acid sequence is 3' of the nucleic acid sequence encoding the ALV surface glycoprotein amino acid sequence such that the ALV surface glycoprotein amino acid sequence and the ALV transmembrane glycoprotein amino acid sequence are translated from the same mRNA molecule. While not being limited to any particular mechanism of action, it is believed that the ALV transmembrane glycoprotein amino acid sequence is cleaved from the ALV surface glycoprotein amino acid sequence during or shortly after translation. In one embodiment, a nucleic acid molecule of the invention can contain an entire env sequence from an ALV with a heterologous amino acid sequence attached to the amino-terminal portion of that env sequence.

Additional nucleic acid sequences can be part of a nucleic acid molecule of the invention. Such additional nucleic acid sequences include, without limitation, retroviral 5'-LTR sequences, retroviral gag sequences, retroviral pol sequences, and retroviral 3'-LTR sequences. For example, a nucleic acid molecule can contain, in the 5' to 3' direction, an ALV 5'-LTR sequence, an ALV gag sequence, an ALV pol sequence, a nucleic acid sequence encoding an ALV surface glycoprotein amino acid sequence with a heterologous amino acid sequence attached to the amino-terminal portion of that ALV surface glycoprotein amino acid sequence, a nucleic acid sequence encoding an ALV transmembrane glycoprotein amino acid sequence, and an ALV 3'-LTR sequence. Other nucleic acid sequences can be included as well. For example, a nucleic acid molecule of the invention can contain a nucleic acid sequence of any length between a retroviral env sequence and a retroviral 3'-LTR sequence. Such nucleic acid sequences can encode a polypeptide and can be heterologous to nucleic acid sequences found in naturally occurring ALV. For example, a nucleic acid located between a retroviral env sequence and a retroviral 3'-LTR sequence can encode a mammalian receptor, a mammalian receptor ligand, an immunoglobulin (e.g., single-chain antibody), an enzyme (e.g., alkaline phosphatase), an enzyme substrate, a growth factor, a cytokine, or a fragment thereof.

The nucleic acid molecules provided herein can be transcribed to form an RNA molecule that encodes a signal polypeptide followed by a protease cleavage site followed by an amino acid sequence heterologous to naturally occurring ALV amino acid sequences followed by an ALV surface glycoprotein amino acid sequence followed by an ALV transmembrane glycoprotein amino acid sequence. In this case, the sequence of the signal polypeptide and protease cleavage site can be encoded by ALV gag and/or ALV env sequences. Once transcribed, the RNA molecule can be translated to form a polypeptide. During or shortly after translation, the heterologous amino acid sequence can be cleaved from the signal polypeptide via cleavage at the cleavage site, and the ALV surface glycoprotein amino acid sequence can be cleaved from the ALV transmembrane glycoprotein amino acid sequence releasing a polypeptide containing the heterologous amino acid sequence attached to the amino-terminal portion of the ALV surface glycoprotein amino acid sequence and lacking the signal polypeptide, the protease cleavage site, and the ALV transmembrane glycoprotein amino acid sequence.

The nucleic acid molecules provided herein can contain ALV nucleic acid sequences such that cells (e.g., avian cells) transfected with the nucleic acid molecule produce infectious virus particles. Typically, such nucleic acid molecules contain, in the 5' to 3' direction, an ALV 5'-LTR sequence, an ALV gag sequence, an ALV pol sequence, a nucleic acid sequence encoding an ALV surface glycoprotein amino acid sequence with a heterologous amino acid sequence attached to the amino-terminal portion of that ALV surface glycoprotein amino acid sequence, a nucleic acid sequence encoding an ALV transmembrane glycoprotein amino acid sequence, and an ALV 3'-LTR sequence. It is noted that little or no ALV surface glycoprotein is shed from infectious ALV particles because ALV surface glycoproteins typically are covalently attached to ALV transmembrane glycoproteins. It also is noted that an additional nucleic acid sequence having a length up to 2.5 kb can be inserted between the nucleic acid sequence encoding an ALV transmembrane glycoprotein amino acid sequence and the ALV 3'-LTR sequence. This additional nucleic acid sequence can encode one or more polypeptides and can be heterologous to nucleic acid sequence found in naturally occurring ALVs. For example, this additional nucleic acid sequence can encode a mammalian receptor, a mammalian receptor ligand, an immunoglobulin, an enzyme (e.g., alkaline phosphatase), or an enzyme substrate.

The nucleic acid molecules provided herein also can contain nucleic acid sequences such that the nucleic acid molecules encode replication-competent retrovirus (e.g., replication-competent ALV). For example, a nucleic acid molecule of the invention can contain viral sequences such that replication-competent retroviruses expressing polypeptides having a heterologous amino acid sequence attached to the amino-terminal portion of an ALV surface glycoprotein amino acid sequence are produced. As described herein, such a nucleic acid molecule can be the ALV(A) retroviral vector containing a nucleic acid sequence encoding a heterologous amino acid sequence that is inserted 5' of the env sequence.

Alternatively, the nucleic acid molecules provided herein can contain nucleic acid sequences such that the nucleic acid molecules encode replication-defective retrovirus (e.g., replication-defective ALV). For example, a nucleic acid molecule of the invention can contain viral sequences such that replication-defective retroviruses expressing polypeptides having a heterologous amino acid sequence attached to the amino-terminal portion of an ALV surface glycoprotein amino acid sequence are produced.

Briefly, vectors encoding replication-competent or replication-defective retroviruses can be produced using standard virology techniques. Such vectors can be based on any ALV, murine leukemia virus (MLV) MLV, spleen necrosis virus (SNV), feline leukemia virus (FeLV), feline immunodeficiency virus (FIV), simian immunodeficiency virus (SIV), human immunodeficiency virus 1 or 2 (HIV-1; HIV-2), or equine infectious anemia virus (EIAV) as well as any other enveloped virus such as herpes simplex viruses (HSV) or measles viruses.

As described herein, ALV surface glycoproteins having amino-terminal polypeptide extensions of various lengths can be efficiently incorporated into infectious virions. In addition, viruses containing ALV surface glycoproteins having amino-terminal polypeptide extensions of various lengths can replicate efficiently, reaching infectious titers comparable to wild-type viruses. Further, viruses containing ALV surface glycoproteins having amino-terminal polypeptide extensions of various lengths (1) can stably retain the amino-terminal polypeptide extensions after repeated virus repassage and (2) can bind both specific immobilized ligands as well as cells expressing specific ligands. Thus, the nucleic acid molecules provided herein can be used to make polypeptide display libraries containing infectious virions that replicate efficiently and stably present polypeptide sequences (e.g., amino acid sequences heterologous to naturally occurring ALV amino acid sequences) that can bind specific molecules such as cell receptors.

Nucleic acid molecules within the scope of the invention can be obtained using any method including, without limitation, common molecular cloning and chemical nucleic acid synthesis techniques. For example, PCR can be used to construct nucleic acid molecules that encode polypeptides where each polypeptide has a different amino acid sequence (e.g., a different non-ALV sequence) attached to the amino-terminal portion of an ALV surface glycoprotein amino acid sequence. PCR refers to a procedure or technique in which target nucleic acid is amplified in a manner similar to that described in U.S. Pat. No. 4,683,195, and subsequent modifications of the procedure described therein.

2. Nucleic Acid Libraries

The invention provides collections of the nucleic acid molecules described herein. For example, the invention provides libraries of different nucleic acid molecules that encode polypeptides where each polypeptide has a different heterologous amino acid sequence (e.g., a different non-ALV sequence) attached to the amino-terminal portion of an ALV surface glycoprotein amino acid sequence. As described herein, each nucleic acid molecule within a library can encode a replication-competent retrovirus (e.g., replication-competent ALV) or a replication-deficient retroviruses (e.g., replication-deficient ALV). Typically, each nucleic acid molecule within a collection contains (1) a nucleic acid sequence that encodes a polypeptide having a different heterologous amino acid sequence attached to the amino-terminal portion of an ALV surface glycoprotein amino acid sequence and (2) viral nucleic acid sequences such that replication-competent retroviruses displaying that polypeptide are produced. In this case, the nucleic acid molecules can be used to create a library of retrovirus particles that (1) display different polypeptides having an ALV surface glycoprotein amino acid sequence with a heterologous amino-terminal extension and (2) contain the nucleic acid molecule that encodes that polypeptide. Thus, retroviruses that display a particular polypeptide having a heterologous amino-terminal extension with a desired activity can be selected and then replicated such that the nucleic acid sequence encoding that polypeptide can be identified.

Again, the invention provides collections of nucleic acid molecules that can be used to generate retroviral polypeptide display libraries where each retroviral particle displays an ALV surface glycoprotein amino acid sequence with a unique heterologous amino-terminal extension. For example, each viral particle can have the same ALV surface glycoprotein amino acid sequence but a different heterologous amino-terminal extension. Typically, the collections of nucleic acid molecules will contain a large number of different nucleic acid molecules. For example, a collection of nucleic acid molecules can contain greater than 500, $10^3$, $10^4$, $10^5$, $10^6$, $10^7$, $10^8$, $10^9$, or $10^{10}$ different nucleic acid molecules. Such collections of nucleic acid molecules can be obtained using standard molecule biology techniques such as molecular cloning and PCR. For example, restriction enzymes can be used to move polypeptide-encoding sequences and fragments of polypeptide-encoding sequences from commercially available expression libraries into retroviral vectors such as ALV(A). In addition, PCR can be used as described in Buchholz et al. (*Nat. Biotech.*, 16:951–954 (1998)) to generate randomized nucleic acid sequences.

Each nucleic acid molecule of a collection of nucleic acid molecules can contain an additional nucleic acid sequence that is (1) heterologous to naturally occurring ALV sequences and (2) is located between an ALV env sequence and an ALV 3'LTR sequence. This additional nucleic acid sequence can be any length and can encode a polypeptide (e.g., an enzyme, cell receptor, or ligand). For example, this additional nucleic acid sequence can be 25, 50, 100, 150, 200, 300, 500, 1000, 1500, 2000, or more nucleotides in length. In addition, this additional nucleic acid sequence can be identical for each nucleic acid molecule of a collection or it can be different for each nucleic acid molecule of a collection. For example, each nucleic acid molecule of a collection of nucleic acid molecules that encodes a polypeptide having a different heterologous amino acid sequence attached to the amino-terminal portion of an ALV surface glycoprotein amino acid sequence can contain an additional nucleic acid sequence that encodes alkaline phosphatase and is located between an ALV env sequence and an ALV 3'LTR sequence. Alternatively, each nucleic acid molecule that encodes a polypeptide having a different heterologous amino acid sequence attached to the amino-terminal portion of an ALV surface glycoprotein amino acid sequence can contain a different additional nucleic acid sequence located between an ALV env sequence and an ALV 3'LTR sequence. In this latter case, the collection of nucleic acid molecules can be considered a combination of two different libraries. One being a library of different amino-terminal extensions, and the other being a library of different additional nucleic acid sequences.

Typically, each nucleic acid molecule within a double-library collection contains (1) a nucleic acid sequence that encodes a polypeptide having a different heterologous amino acid sequence attached to the amino-terminal portion of an ALV surface glycoprotein amino acid sequence, (2) an additional nucleic acid sequence located between an ALV env sequence and an ALV 3'LTR sequence, where the additional nucleic acid sequence is heterologous to naturally occurring ALV sequences and encodes a polypeptide, and (3) viral nucleic acid sequences such that replication-competent retroviruses expressing both polypeptides are produced. In this case, the nucleic acid molecules can be used to create a library of retrovirus particles that (1) display different polypeptides having an ALV surface glycoprotein amino acid sequence with a heterologous amino-terminal extension, (2) express different heterologous polypeptides that are not attached to an ALV surface glycoprotein amino acid sequence, and (3) contain a nucleic acid molecule that encodes both polypeptides. Thus, retroviruses that exhibit a desired activity as a result of expressing particular combinations of the two varied polypeptides can be selected and then replicated such that the nucleic acid sequences encoding those two polypeptides can be identified.

3. Polypeptides and Polypeptide Libraries

The invention provides polypeptides having an ALV surface glycoprotein amino acid sequence with a heterologous amino-terminal extension. Polypeptides having an ALV surface glycoprotein amino acid sequence with a heterologous amino-terminal extension can be substantially pure. The term "substantially pure" as used herein with reference to a polypeptide means the polypeptide is substantially free of other polypeptides, lipids, carbohydrates, and nucleic acid. Thus, a substantially pure polypeptide is any polypeptide that is at least about 65, 70, 75, 80, 85, 90, 95, or 99 percent pure. Typically, a substantially pure polypeptide will yield a single major band on a non-reducing polyacrylamide gel.

Any method can be used to obtain a polypeptide. For example, common polypeptide purification techniques such as affinity chromatography and HPLC as well as polypeptide synthesis techniques can be used. In addition, any material can be used as a source to obtain a polypeptide within the scope of the invention. For example, a retrovirus described herein can be selected for having a desired activity and replicated so that the nucleic acid sequence encoding the polypeptide responsible for that desired activity is identified. Once identified, the nucleic acid sequence can be used to produce a polypeptide preparation. This resulting polypeptide preparation can then be used to study the desired activity, to produce antibodies, or to identify agonists or antagonists of the desired activity.

The invention also provides collections of the polypeptides described herein. For example, the invention provides libraries of different polypeptides where each polypeptide has a different heterologous amino acid sequence (e.g., a different non-ALV sequence) attached to the amino-terminal portion of an ALV surface glycoprotein amino acid sequence. Typically, the collections of polypeptides will contain a large number of different polypeptides. For example, a collection of polypeptides can contain greater than 500, $10^3$, $10^4$, $10^5$, $10^6$, $10^7$, $10^8$, $10^9$, or $10^{10}$ different polypeptides. Such collections of polypeptides can be obtained, for example, by cleaving surface polypeptides from retroviral particles that display a polypeptide having an ALV surface glycoprotein amino acid sequence with a heterologous amino-terminal extension.

4. Viruses and Virus Libraries

The invention provides viruses, each virus containing a nucleic acid molecule that encodes a polypeptide having an ALV surface glycoprotein amino acid sequence with a heterologous amino-terminal extension. Viruses containing such nucleic acid molecules are not required to express the encoded polypeptide. Nevertheless, such viruses typically express the encoded polypeptide. For example, an ALV containing a nucleic acid molecule that encodes a polypeptide having an ALV surface glycoprotein amino acid sequence with a heterologous amino-terminal extension can display the encoded polypeptide on the surface of its particle.

Any virus can contain a nucleic acid molecule that encodes a polypeptide having an ALV surface glycoprotein amino acid sequence with a heterologous amino-terminal extension. Such viruses include, without limitation, retroviruses such as ALVs, MLVs, SNVs, FeLVs, FIVs, SIVs, HIV-1, HIV-2, and EIAVs as well as other enveloped viruses such as HSVs and measles viruses. Viruses containing a nucleic acid molecule that encodes a polypeptide having an ALV surface glycoprotein amino acid sequence with a heterologous amino-terminal extension can be replication-competent or replication-defective. In addition, the nucleic acid molecule within the virus can contain any of the nucleic acid sequences described herein. For example, a retrovirus can contain a nucleic acid molecule having (1) a nucleic acid sequence that encodes a polypeptide having an ALV surface glycoprotein amino acid sequence with a heterologous amino-terminal extension and (2) an additional nucleic acid sequence located between an ALV env sequence and an ALV 3'LTR sequence, where the additional nucleic acid sequence is heterologous to naturally occurring ALV sequences and encodes a polypeptide. The viruses described herein can lack Src viral sequences.

Any method can be used to identify viruses containing a nucleic acid molecule of the invention. Such methods include, without limitation, PCR and nucleic acid hybridization techniques such as Northern and Southern analysis. In some cases, immunohistochemistry and biochemical techniques can be used to determine if a virus contains a particular nucleic acid molecule by detecting the expression of a polypeptide encoded by that particular nucleic acid molecule.

The invention also provides viruses, each virus containing a polypeptide having (1) an ALV surface glycoprotein amino acid sequence and (2) an amino acid sequence heterologous to any naturally occurring ALV amino acid sequence. Viruses containing such polypeptides are not required to contain nucleic acid molecules that encode the polypeptide. For example, cell lines that express a polypeptide having an ALV surface glycoprotein amino acid sequence with a heterologous amino-terminal extension can be used to make viruses that display that polypeptide without containing a nucleic acid sequence that encodes it. Nevertheless, a virus containing a polypeptide having an ALV surface glycoprotein amino acid sequence with a heterologous amino-terminal extension typically will contain a nucleic acid molecule that encodes that polypeptide. For example, an ALV containing a polypeptide having an ALV surface glycoprotein amino acid sequence with a heterologous amino-terminal extension displayed on the surface of its particle typically contains a nucleic acid sequence that encodes that polypeptide.

Any virus can contain a polypeptide having an ALV surface glycoprotein amino acid sequence with a heterologous amino-terminal extension. Such viruses include, without limitation, retroviruses such as ALVs, MLVs, SNVs, FeLVs, FIVs, SIVs, HIV-1, HIV-2, and EIAVs as well as other enveloped viruses such as HSVs and measles viruses. Viruses containing a polypeptide having an ALV surface glycoprotein amino acid sequence with a heterologous amino-terminal extension can be replication-competent or replication-defective. In addition, the nucleic acid molecule within the virus can contain any of the nucleic acid sequences described herein. For example, a retrovirus can contain (1) a polypeptide having an ALV surface glycoprotein amino acid sequence with a heterologous amino-terminal extension and (2) a nucleic acid sequence located between an ALV env sequence and an ALV 3'LTR sequence, where the nucleic acid sequence is heterologous to naturally occurring ALV sequences and encodes a polypeptide. The viruses described herein can lack Src viral sequences.

Any method can be used to identify viruses containing a polypeptide of the invention. Such methods include, without limitation, immunohistochemistry and biochemical techniques.

The invention also provides collections of any of the viruses described herein. For example, the invention provides libraries of different viruses that display polypeptides where each polypeptide has a different heterologous amino acid sequence attached to the amino-terminal portion of an ALV surface glycoprotein amino acid sequence. As described herein, each virus within a library can be a replication-competent retrovirus (e.g., replication-competent ALV) or a replication-deficient retrovirus (e.g., replication-deficient ALV). Typically, each virus within a collection (1) displays a polypeptide having a different heterologous amino acid sequence attached to the amino-terminal portion of an ALV surface glycoprotein amino acid sequence on the surface of its particle and (2) contains a nucleic acid sequence that encodes the displayed polypeptide. Thus, retroviruses that display a particular polypeptide having a heterologous amino-terminal extension with a desired activity can be selected and then replicated such that the nucleic acid sequence encoding that polypeptide can be identified.

The collections of viruses can contain a large number of different viruses. For example, an ALV polypeptide display library can contain greater than 500, $10^3$, $10^4$, $10^5$, $10^6$, $10^7$, $10^8$, $10^9$, or $10^{10}$ different members. Such collections of viruses can be obtained using the techniques described herein. For example, PCR can be used as described in Buchholz et al. (*Nat. Biotech.*, 16:951–954 (1998)) to generate randomized nucleic acid sequences that are inserted into the amino-terminal portion of an ALV glycoprotein amino acid sequence. The resulting nucleic acid molecules can then be cloned into a retroviral vector. The resulting retroviral vectors can be transfected into cells such that retroviral particles are produced.

5. Methods for Obtaining Displayed Polypeptide Sequences

The invention provides methods for obtaining displayed polypeptide sequences that interact with biological molecules (e.g., cell receptors and cell glycoproteins) and/or cells (e.g., cancer cells). Such methods include (1) contacting a sample with one of the collections of viruses described herein and (2) isolating any virus that binds to a component within the sample. For example, an ALV polypeptide display library containing greater than $10^5$ replication-competent ALVs where each virus displays an ALV surface glycoprotein having a different heterologous amino-terminal extension can be incubated with a sample. The sample can be any type of biological sample such as immobilized polypeptides or cultured cells. Other examples of samples that can be used include, without limitation, cell suspensions, primary cultures, tissue sections, tissue dissections, cell homogenates, crude polypeptide preparations, purified polypeptide preparations, and carbohydrate preparations. When using cells, the cells can be of any type and can be in vitro or in vivo. For example, a cellular sample can contain cancer cells, liver cells, neurons, lymphocytes, endothelial cells, skin cells, dendritic cells, macrophages, and/or stem cells. It is noted that a cellular sample can contain a collection of different cells (e.g., a mixture of lymphocytes and polymorphonuclear cells) or can contain cells of the same type (e.g., a clonal culture of cancer cells). Examples of cancer cells that can be used include, without limitation, head and neck cancer cells, breast cancer cells, prostate cancer cells, lung cancer cells, colorectal cancer cells, pancreas cancer cells, glioma cells, lymphoma cells, myeloma cells, and leukemia cells.

Any method can be used to isolate viruses that bind a component within a sample. For example, viruses bound to an immobilized polypeptide preparation can be isolated by (1) washing the preparation to remove any unbound viruses, (2) adding cells known to be susceptible to viral infection to the preparation, and (3) harvesting viral particles that were amplified as a result of viral infection. Once harvested, the viruses can be evaluated to determine the particular nucleic acid sequence that encoded the displayed polypeptide responsible for the binding activity.

When using cells in vitro or in vivo, the cells can be cells that do not express receptors for the wild-type viruses. In the case of ALV, wild-type ALV do not infect mammalian cells since mammalian cells do not express receptors for ALV. Thus, the infectious ALV polypeptide display libraries provided herein can be incubated with mammalian cells to identify displayed polypeptide sequences that allow ALVs to infect the mammalian cells. For example, the ALV viruses provided herein can be incubated with mammalian cells. After incubation, viruses that infected the mammalian cells can be isolated by (1) washing the cells to remove any unbound viruses and (2) harvesting viral particles that were amplified as a result of viral infection. Once harvested, the viruses can be evaluated to determine the particular nucleic acid sequence that encoded the displayed polypeptide responsible for the virus particle's ability to infect the mammalian cells.

Many other methods and techniques can be used to identify displayed polypeptide sequences having a desired activity. In fact, the methods and techniques commonly used with phage display libraries can be employed using the viruses and viral polypeptide display libraries provided herein. For example, the viruses and viral polypeptide display libraries provided herein can be in a manner similar to the phage display libraries described elsewhere (Arap et al., *Science*, 279:377–380 (1998); Ellerby et al., *Nature Med.*, 5:1032–1038 (1999); Pasqualini and Ruoslahti, *Nature*, 380:364–366 (1996); Rajotte et al., *J. Clin. Invest.*, 102:430–437 (1998); and Trepel et al., *Hum. Gene Ther.*, 11:1971–1981 (2000)).

Once a particular displayed polypeptide having a desired activity has been identified, any biological molecule (e.g., cell receptors and cell glycoproteins) that interacts with that displayed polypeptide can be identified. For example, the displayed polypeptide sequence that allows an ALV to infect a mammalian cancer cell can be isolated or synthesized to obtain a substantially pure polypeptide preparation. That substantially pure polypeptide preparation can be used to isolate the molecule that interacts with it via, for example, affinity chromatography. In addition, any of the common molecular biology techniques such as expression cloning and yeast two-hybrid systems can be using to identify polypeptides that interact with displayed polypeptides. For example, the methods described in Smith and Petrenko (*Chem. Rev.*, 97:391–410 (1997)) and Rajotte and Ruoslahti (*J. Biol. Chem.*, 274:11593–11598 (1999) can be used to obtain a polypeptide that specifically interacts with a particular displayed polypeptide sequence. It is noted that a substantially pure polypeptide preparation of a displayed polypeptide sequence can be used to produce antibodies. Such antibodies can be used to help identify polypeptides that interact with displayed polypeptides.

The invention will be further described in the following examples, which do not limit the scope of the invention described in the claims.

EXAMPLES

Example 1

Figure 1:
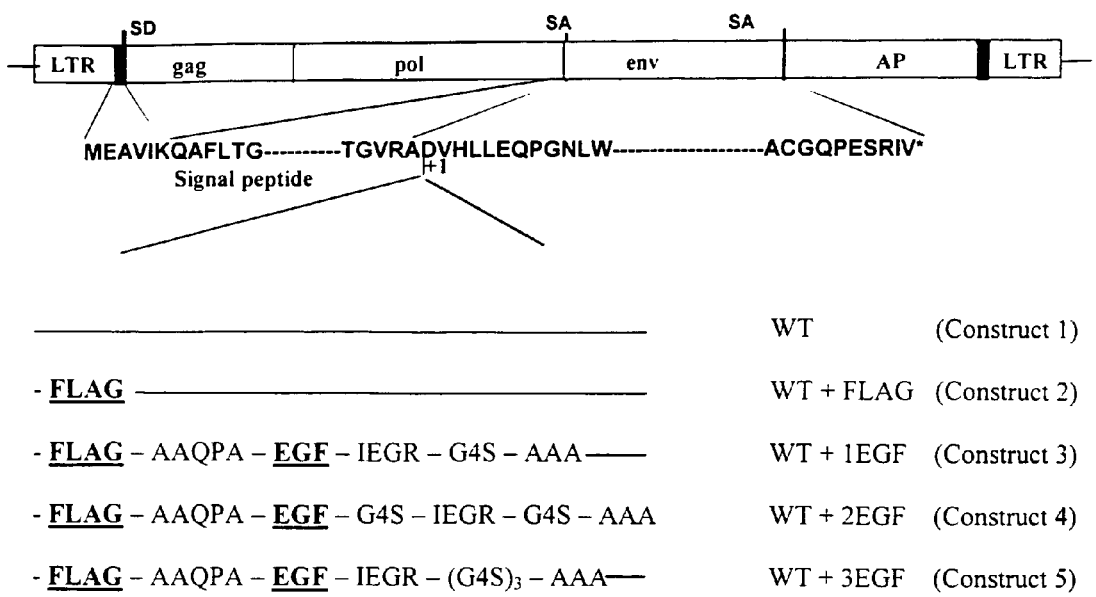
FIG. 1 is a schematic representation of the ALV(A) retroviral vector, the wild-type construct 1, and the chimeric envelope glycoprotein constructs 2–5. The ALV-based retroviral vector contains the gag, pol, and env viral sequences and nucleic acid encoding an alkaline phosphatase polypeptide flanked by long terminal repeats (LTR). The envelope glycoproteins are translated from a spliced mRNA and contain a signal peptide (including six amino acids from the start of Gag) followed by a protease cleavage site at the start of the mature surface glycoprotein (+1). All chimeric envelope glycoproteins contained additional epitopes inserted in frame at the amino-terminus of the env sequence (+1). The bolded and underlined FLAG represents the eight amino acid FLAG® epitope; the bolded and underlined EGF represents a 53-amino acid EGF ligand; and the G4S represents four glycine residues followed by a serine residue. The AAQPA (SEQ ID NO:8), IEGR (SEQ ID NO:9), and AAA sequences represent the amino acid sequences of an Sfi I site, a Factor Xa cleavage site, and a Not I site, respectively. The SD represents a splice donor, while the SA represents a splice acceptor.

Infectious ALV Molecular Clones with Envelope Glycoproteins Having Additional Polypeptide Epitopes as N-terminal Extensions Five constructs were generated from the ALV(A) retroviral vector RCASBP(A)AP. This vector is described elsewhere (Federspiel and Hughes, Retroviral gene delivery. In: Muscle: Methods for Cell and Muscle Research, Eds. Emerson and Sweeney, Academic Press. pp. 179–214 (1997)). Construct 1 contained, in the 5' to 3' direction, the ALV(A) retroviral 5' LTR, the gag, pol, and env viral sequences, a nucleic acid sequence encoding an alkaline phosphatase (AP) polypeptide, and the ALV(A) retroviral 3' LTR. Constructs 2, 3, 4, and 5 were identical to construct 1 with the exception that each contained an additional nucleic acid sequence that was inserted, in frame, at the 5' end of the env viral sequence (FIG. 1). For construct 2, the inserted nucleic acid sequence encoded a FLAG® epitope (DYKDDDDK; SEQ ID NO:7). For construct 3, the inserted nucleic acid sequence was, in the 5' to 3' direction, (1) a sequence that encoded a FLAG® epitope, (2) a sequence recognized by the SfiI restriction enzyme and encoding AAQPA (SEQ ID NO:8), (3) a sequence encoding a 53-amino acid EGF ligand, (4) a sequence encoding a Factor Xa cleavage site (IEGR; SEQ ID NO:9), (5) a sequence encoding a G4S linker (GGGGS; SEQ ID NO:10), and (6) a sequence recognized by the NotI restriction enzyme and encoding AAA. For construct 4, theinserted nucleic acid sequence was, in the 5' to 3' direction, (1) a sequence that encoded a FLAG® epitope, (2) a sequence recognized by the SfiI restriction enzyme and encoding AAQPA (SEQ ID NO:8), (3) a sequence encoding a 53-amino acid EGF ligand, (4) a sequence encoding a G4S linker, (5) a sequence encoding a Factor Xa cleavage site, (6) a sequence encoding a G4S linker, and (7) a sequence recognized by the NotI restriction enzyme and encoding AAA. For construct 5, the inserted nucleic acid sequence was, in the 5' to 3' direction, (1) a sequence that encoded a FLAG® epitope, (2) a sequence recognized by the SfiI restriction enzyme and encoding AAQPA (SEQ ID NO:8), (3) a sequence encoding a 53-amino acid EGF ligand, (4) a sequence encoding a Factor Xa cleavage site, (5) a sequence encoding three G4S linkers in tandem, and (6) a sequence recognized by the NotI restriction enzyme and encoding AAA.

The nucleic acid sequence encoding the FLAG® epitope, an eight amino acid polypeptide sequence, was included so that virus particles displaying the FLAG® epitope as an N-terminal extension of the ALV surface glycoprotein could be detected using, for example, anti-FLAG® epitope antibodies. Likewise, the nucleic acid sequence encoding the EGF ligand, a 53-amino acid polypeptide sequence, was included so that virus particles displaying a properly folded EGF ligand as an N-terminal extension of the ALV surface glycoprotein could be detected using, for example, anti-EGF ligand antibodies. The Factor Xa protease cleavage site was included to help demonstrate the presence of the appropriate epitopes since Factor Xa could be used to cleave the polypeptide extensions from the remaining envelope sequence. Each construct also contains a sequence encoding an AP polypeptide to aid in monitoring virus replication and in quantifying viral titers.

Figure 2:
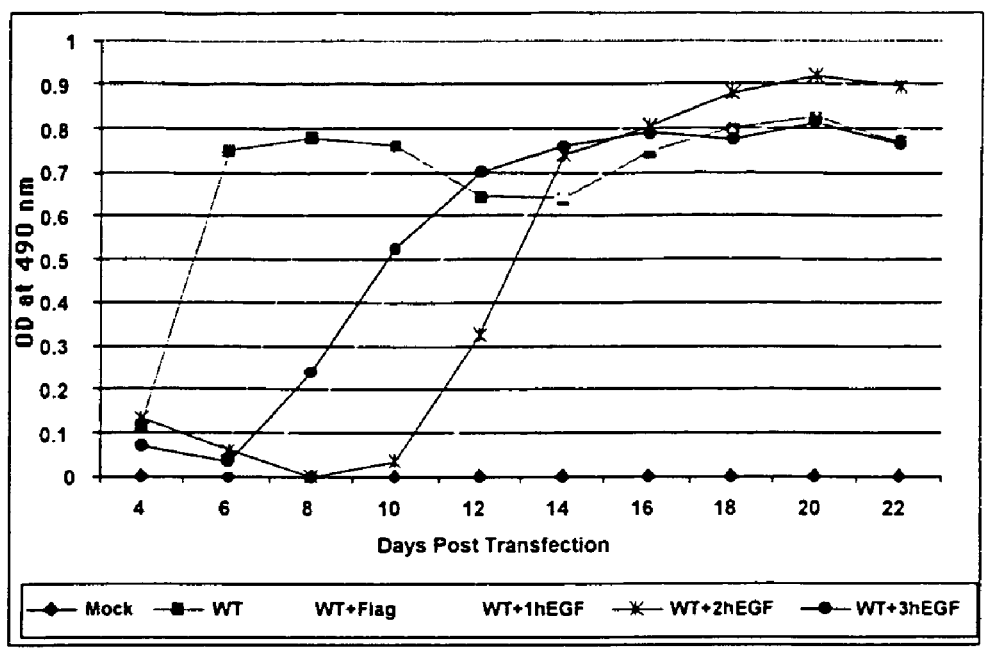
FIG. 2 is a graph plotting virus growth ($OD_{490}$) versus days post transfection for viruses produced from cells either mock transfected or transfected with the indicated construct.

To determine if the N-terminal extensions of the envelope glycoproteins could be tolerated in replicating viruses, plasmid DNA containing the infectious molecular clones (constructs 1–5) was transfected into separate cultures of chicken fibroblast DF-1 cells, and the cultures were passaged to allow virus production and spread. The four constructs (constructs 2–5) containing N-terminal extensions resulted in infectious virus production although possibly at a slower rate compared to the production using the wild-type construct (construct 1; FIG. 2). In addition, the titers of the infectious viruses was determined by serial dilution of day 20 culture supernatants. Briefly, the serially diluted supernatants were used to infect fresh DF-1 cells. After two days, the number of AP-positive cells was determined. The titer for the viruses from the wild-type construct (construct 1) was $5 \times 10^6$ infectious units per mL (ifu/mL), while the titers for the viruses from all four chimeric constructs (constructs 2–5) were $1 \times 10^6$ ifu/mL. These results demonstrate that ALV viruses with envelope glycoproteins having non-viral N-terminal polypeptide extensions can replicate efficiently, reaching infectious titers comparable to wild-type ALV viruses.

The following experiments were performed to determine whether the chimeric envelope glycoproteins were efficiently incorporated into ALV virions. ALV virions were pelleted from 3 mL of culture supernatants obtained from 20 day cultures. The polypeptides were denatured, separated by 12% SDS-PAGE, and analyzed by Western immunoblot. The filters were probed with either an anti-FLAG® epitope monoclonal antibody (1:2000 dilution; Sigma, St. Louis, Mo.), an anti-human EGF monoclonal antibody (1.0 µg/mL; R & D Systems Inc., Minneapolis, Minn.), or rabbit anti-ALV CA polyclonal sera (1:5000 dilution; Charles River/ SPAFAS, North Franklin, Conn.). The rabbit anti-ALV CA polyclonal sera recognize the ALV capsid. The bound antibodies were probed with either an anti-mouse or anti-rabbit antibody conjugated to horse-radish peroxidase (HRP). Any resulting immunocomplexes were visualized by chemiluminescence. On Western immunoblots, the estimated size of the construct 1 surface glycoprotein and the construct 2 surface glycoprotein was ~80 kDa; the estimated size of the EGF containing surface glycoproteins from constructs 3, 4, and 5 was ~90 kDa; and the estimated size of the ALV capsid for each ALV was ~26 kDa.

Figure 3:
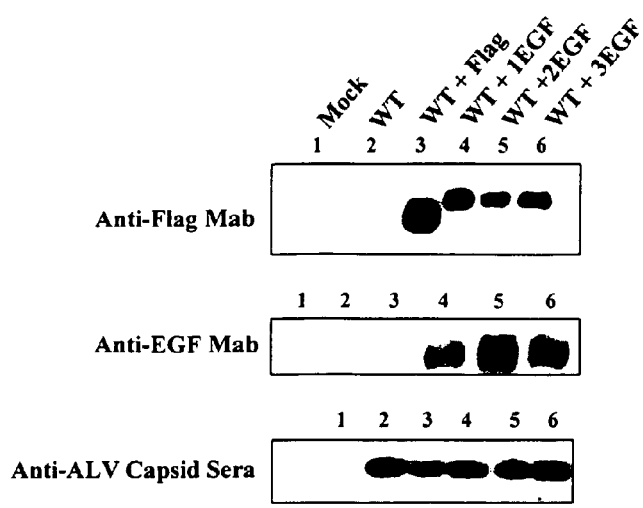
FIG. 3 contains photographs from Western immunoblots performed using the indicated antibodies. In each case, lane 1 contained a sample made from a mock transfection; lane 2 contained a sample made using WT ALV(A) (construct 1); lane 3 contained a sample made using WT+FLAG (construct 2); lane 4 contained a sample made using WT+1EGF (construct 3); lane 5 contained a sample made using WT+2EGF (construct 4); and lane 6 contained a sample made using WT+3EGF (construct 5).

Western immunoblot analysis of viral particles produced by the DF-1 cell cultures demonstrated that the chimeric envelope glycoproteins were incorporated into virions (FIG. 3). In addition, the envelope glycoproteins containing the FLAG® and EGF epitopes (envelope glycoproteins encoded by constructs 3, 4, and 5) were larger on the immunoblots than the envelope glycoproteins containing the FLAG® epitope and not the EGF epitope (envelope glycoproteins encoded by construct 2).

The following experiment was performed to confirm that the chimeric envelope glycoproteins were incorporated into virions and to determine whether the chimeric envelope glycoproteins were sensitivity of to Factor Xa protease digestion. Virions were pelleted as described above, resuspended in OPTI-MEM (GIBCO/BRL), and digested with or without Factor Xa protease (100 µg/mL; New England Biolabs, Inc.; Beverly, Mass.) at 37° C. for 90 minutes. After digestion, the samples were denatured, separated by 12%

Figure 4:
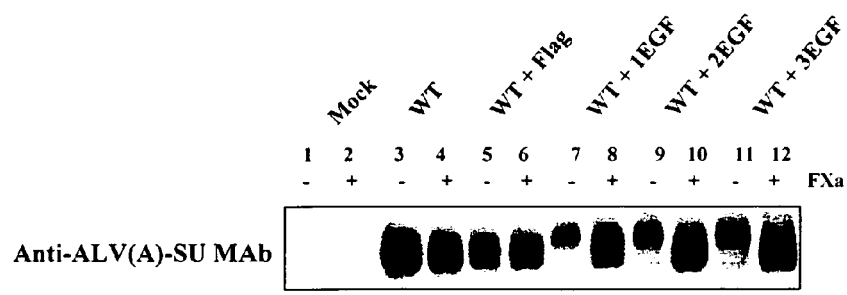
FIG. 4 contains a photograph from a Western immunoblot performed using the indicated antibody and sample treated with (+) or without (−) Factor Xa. Lanes 1 and 2 contained a sample made from a mock transfection; lanes 3 and 4 contained a sample made using WT ALV(A) (construct 1); lanes 5 and 6 contained a sample made using WT+FLAG (construct 2); lanes 7 and 8 contained a sample made using WT+1EGF (construct 3); lanes 9 and 10 contained a sample made using WT+2EGF (construct 4); and lanes 11 and 12 contained a sample made using WT+3EGF (construct 5).
Figure 5:
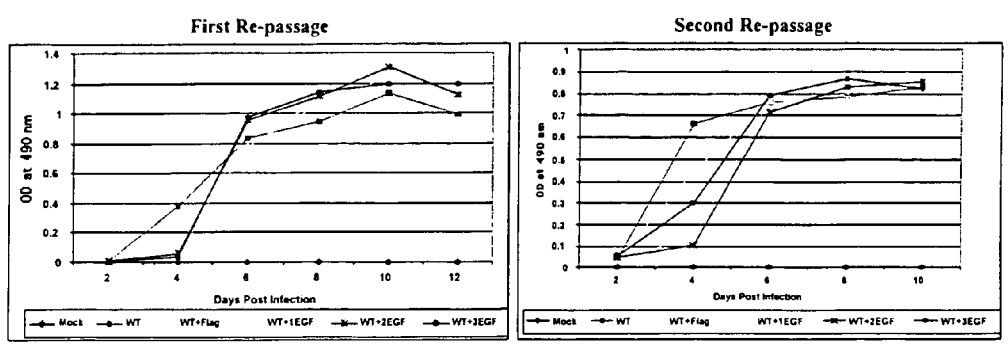
FIG. 5 contains graphs plotting virus growth ($OD_{490}$) versus days post infection for first and second re-passages of viruses produced from cells either mock transfected or transfected with the indicated construct.

SDS-PAGE, and analyzed by Western immunoblot probed with an anti-ALV(A) SU monoclonal antibody. The bound immunocomplexes were visualized by chemiluminescence. For each surface glycoprotein containing the 53-amino acid EGF epitope, a shift in size was detectable after Factor Xa digestion (FIG. 4). No shift was detected in surface glycoproteins from construct 1. Likewise, given the size of the FLAG® epitope, no shift was detected in surface glycoproteins from construct 2. These results demonstrate that the N-terminal extensions were accessible to Factor Xa protease cleavage.

The following experiments were performed to determined whether the chimeric envelope glycoproteins were stable after repeated virus re-passage. Stability of the displayed epitopes on ALV glycoproteins is important when ALV is to be used as a polypeptide display platform since most selection protocols will involve the amplification of the viruses that bound to a target. Virus stocks produced by transfecting DF-1 cells with the infectious clone DNA were re-passaged in DF-1 cells after a low MOI infection. Specifically, two rounds of re-passage in DF-1 cells were performed. For the first re-passage, DF-1 cells were infected with virus stocks from 20-day primary cultures at an MOI of 0.001. For the second re-passage, DF-1 cells were infected with virus stocks from 12-day cultures from the first re-passage at an MOI of 0.001. In each case, virus replication was monitored by ELISA using the rabbit anti-ALV CA polyclonal sera. Virus replication was observed during both the first and the second re-passage for each of the construct-containing ALV viruses. As expected, no virus replication was observed in mock treated cultures.

Figure 6:
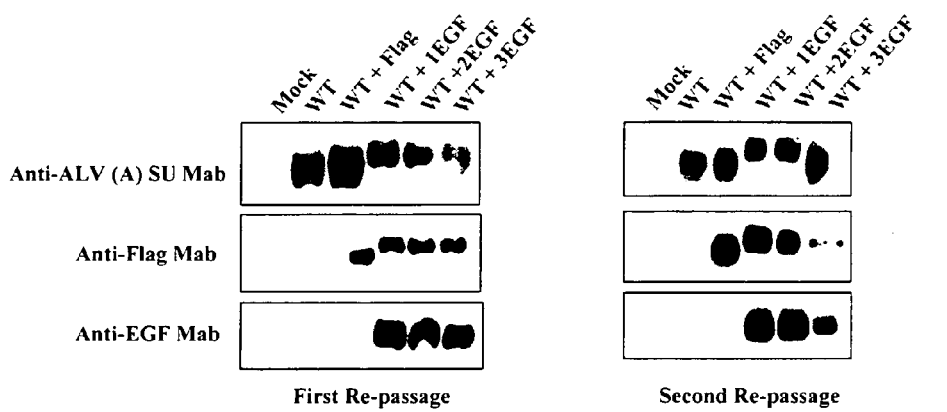
FIG. 6 contains photographs from Western immunoblots performed using the indicated antibodies and samples obtained from either first or second re-passages. In each case, lane 1 contained a sample made from a mock transfection; lane 2 contained a first or second re-passage sample made using WT ALV(A) (construct 1); lane 3 contained a first or second re-passage sample made using WT+FLAG (construct 2); lane 4 contained a first or second re-passage sample made using WT+1EGF (construct 3); lane 5 contained a first or second re-passage sample made using WT+2EGF (construct 4); and lane 6 contained a first or second re-passage sample made using WT+3EGF (construct 5).

In addition, virion glycoproteins produced by the first and second re-passage cultures were analyzed by Western immunoblot using the anti-ALV(A) SU monoclonal antibody, the anti-FLAG® epitope monoclonal antibody, and the anti-human EGF monoclonal antibody (FIG. 6). Using the anti-ALV(A) SU monoclonal antibody, virion glycoproteins were detected for each tested sample (ALV from constructs 1–5) for both the first and second re-passages. Using the anti-FLAG® epitope monoclonal antibody, virion glycoproteins were detected for each tested sample expected to contain the FLAG® epitope (ALV from constructs 2–5) for both the first and second re-passages. Using the anti-human EGF monoclonal antibody, virion glycoproteins were detected for each tested sample expected to contain the EGF epitope (ALV from constructs 3–5) for both the first and second re-passages. For construct 5-containing viruses, a population of viruses lacking the FLAG® and EGF epitopes appeared to be selected over time. From this analysis, at least three of the four tested viruses stably displayed the FLAG® epitope or the FLAG®/EGF epitopes through both re-passages.

To determine if the displayed non-viral epitopes on ALV (A) surface glycoproteins are accessible to bind target proteins, wild-type virions (from construct 1) and chimeric virions (from constructs 2–5) were exposed to tissue culture wells coated with either anti-FLAG® or anti-EGF monoclonal antibodies. Briefly, tissue culture wells were coated with the anti-FLAG® monoclonal antibody (0.5 µg/mL), washed with phosphate buffered saline (PBS) with 0.1% Tween-80, and blocked with PBS with 5% fetal calf serum (FCS). Virus stocks produced by DF-1 cells transfected with constructs 1–5 were incubated in the blocked wells at 4° C. for 60 minutes. After washing the wells three times with PBS, DF-1 cells were added, and the plates were incubated at 39° C. for 2 days. The cells were then fixed with 4% paraformadehyde and assayed for AP activity. Dark blue/purple cells were positive for AP activity.

AP activity was detected in the wells coated with the anti-FLAG® epitope monoclonal antibodies and containing the virions made from constructs 2–5. Thus, the virions made from constructs 2–5 contained the FLAG® epitope, bound to the wells coated with anti-FLAG® epitope antibodies, and infected the DF-1 cells. AP activity also was detected in the wells coated with the anti-EGF epitope monoclonal antibodies and containing the virions made from constructs 3–5. Thus, the virions made from constructs 3–5 contained the EGF epitope, bound to the wells coated with anti-EGF epitope antibodies, and infected the DF-1 cells. No AP activity was detected in mock controls. These mock controls were cells that were not infected but were subjected to all the assay procedures. The results demonstrated that the FLAG® and EGF epitopes displayed on the virion glycoproteins were accessible to specific binding by the appropriate antibody immobilized on a solid support.

Figure 7:
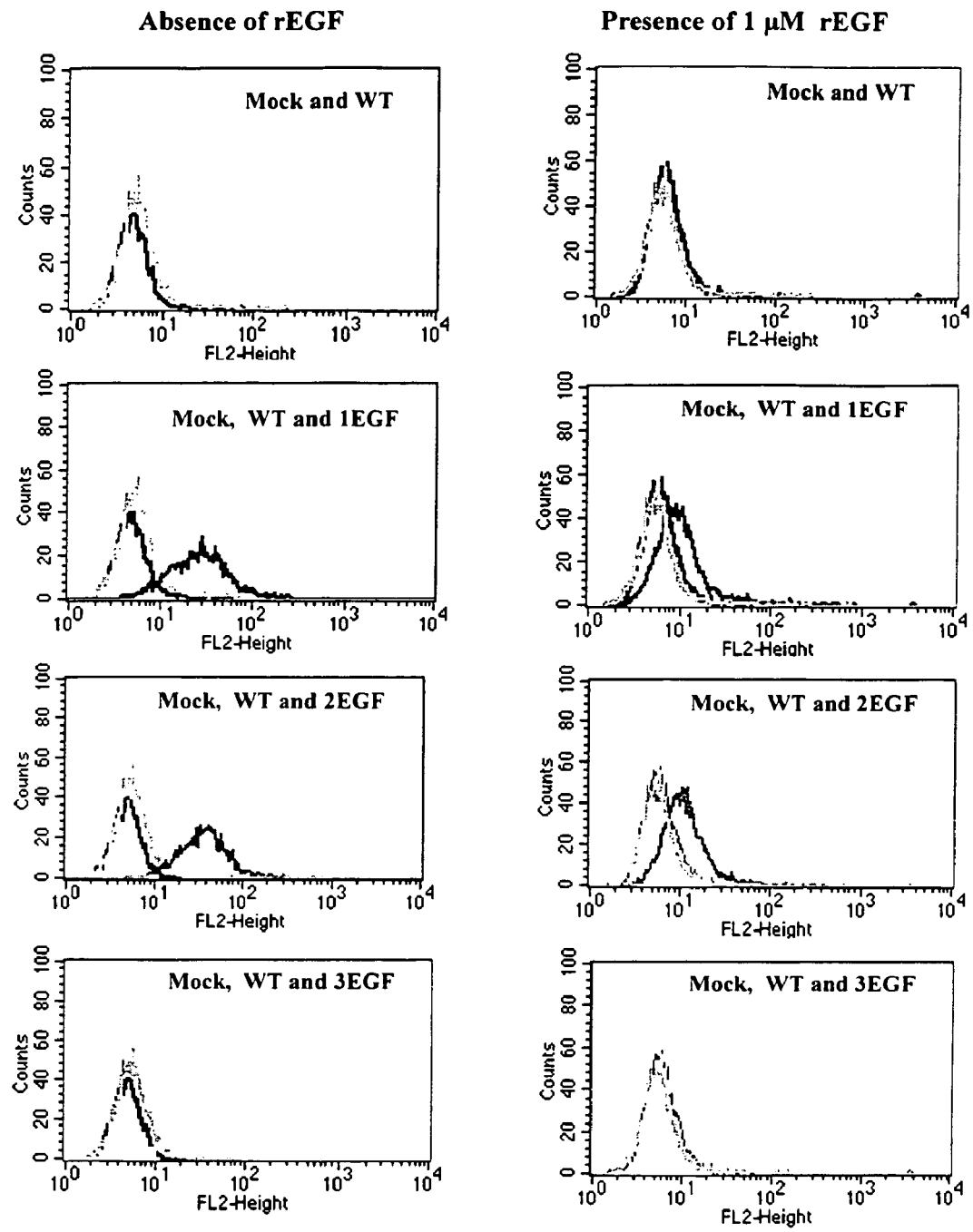
FIG. 7 is eight FACS graphs plotting cell counts versus fluorescence (FL2-Height) for A431 cells incubated with viruses made using the indicated constructs either in the presence or absence of 1 μM recombinant EGF.

A concern about polypeptide display on an enveloped virus is the potential problem of the virions non-specifically binding to eukaryotic cells. To address this concern and determine if the ALV(A) virions display a functional EGF ligand, wild-type (made from construct 1) and chimeric virions (made from constructs 2–5) were incubated with the human tumor cell line A431. This cell line expresses high levels of the human EGF receptor. Briefly, virus stocks were concentrated by centrifugation (1:10). The concentrated stocks were then incubated with $1 \times 10^6$ A431 cells in suspension (total volume 4 mL) at 4° C. for 1 hour. The virus:cell complexes were washed three times with PBS containing 2% FCS and then incubated with the soluble chicken ALV(A) receptor Tva fused to a mouse IgG (sTva-mIgG). sTva-mIgG binds specifically to ALV(A) surface glycoproteins. After washing the complexes three times with PBS containing 2% FCS, the complexes were incubated with anti-mouse IgG conjugated to phycoerythrin, washed, resuspended in PBS containing 2% FCS, and analyzed with a Becton Dickinson FACSCalibur using CELLQuest 3.1 software. Only the viruses displaying the EGF ligand bound to the A431 cells (FIG. 7). In addition, the binding was specific for the human EGF receptor since addition of 1 µM recombinant EGF (rEGF) significantly reduced virus binding. These results demonstrate that ALV(A) virions displaying the human EGF ligand specifically bind to cells expressing the human EGF receptor.

Taken together, these data demonstrate that viruses displaying chimeric envelope glycoproteins can be produced in high titers, and that they retain their infectivity through multiple passages. In addition, these data demonstrate that epitopes within displayed chimeric envelope glycoproteins are accessible and functional. Further, these data demonstrate the feasibility of using chimeric envelope glycoproteins to deliver or match a virus to a particular target.

Example 2

Generating an ALV Peptide Display Library

The following experiments are performed to generate and characterize ALV polypeptide display libraries containing a diverse array of unglycosylated and/or glycosylated polypeptides. At least three different libraries of polypeptides, 10 to 12 amino acid residues in length, are produced having either a randomized residues at all positions, randomized residues at all positions with a fixed N-linked glycosylation site, or randomized residues at all positions with a fixed N-linked glycosylation site flanked by cysteine residues to produce cyclic peptides. The assembly of such libraries can lead to the generation of polypeptides having novel and more diverse binding properties. In fact, using 10 to 12 residue polypeptides can increase the potential of creating unique binding motifs when compared to shorter polypeptides.

Figure 9:
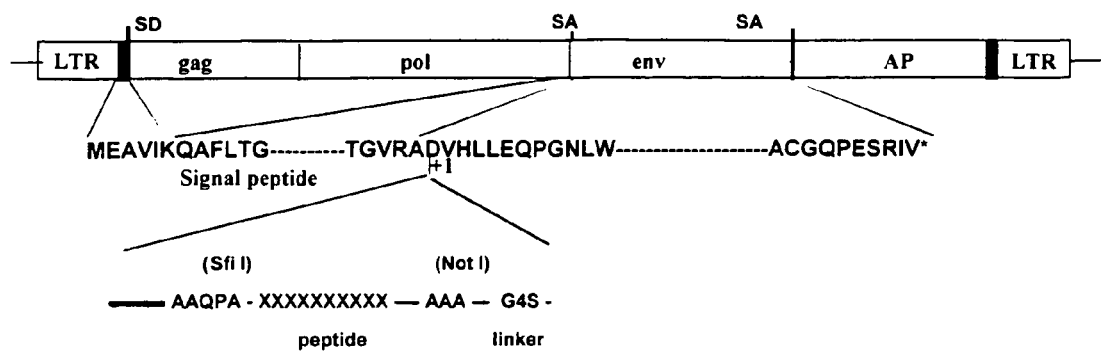
FIG. 9 is a schematic representation of the ALV(A) retroviral vector of an ALV library designed to contain linear 10-mer polypeptides, $X_{10}$, randomized at all positions. The AAQPA (SEQ ID NO:8) and AAA sequences represent the amino acid sequences of an Sfi I site and a Not I site, respectively. The G4S represents four glycine residues followed by a serine residue. The SD represents a splice donor, while the SA represents a splice acceptor.

Briefly, polypeptide libraries are generated and characterized in plasmids that contain the infectious molecular clone of ALV(A). Then, the plasmid polypeptide library is used to produce the virus library (FIG. 8). The organization of the displayed polypeptides on the ALV(A) surface glycoprotein is slightly different when compared to the organization of constructs 3–5. Each polypeptide is displayed on replicating ALV(A) particles as N-terminal extensions of the viral surface envelope glycoproteins with a G4S linker being located between the N-terminal extensions and surface envelope glycoprotein sequence (FIG. 9). In addition, each polypeptides is encoded by nucleic acid sequences located between SfiI and NotI cloning sites.

One library is designed to contain linear 10-mer polypeptides, $X_{10}$, randomized at all positions. A second library is designed to contain linear 12-mer polypeptides of the general format, $X_2NXTX_7$ (SEQ ID NO:16) or $X_2NXSX_7$ (SEQ ID NO:17), where the NXT or NXS represents a fixed N-linked glycosylation signal of three amino acids (asparagine-X-threonine or asparagine-X-serine). A third library is designed to contain cyclic glycosylated polypeptides of the same general format as the second library but containing fixed cysteines as follows: $CX_2NXTX_7C$ (SEQ ID NO:11) or $CX_2NXSX_7C$ (SEQ ID NO:12).

PCR randomization of the base nucleotide sequence is used to construct the polypeptide libraries as described elsewhere (Buchholz et al., *Nat. Biotech.*, 16:951–954 (1998)). Briefly, an oligonucleotide primer that contains the unique KpnI site just upstream of the env splice acceptor site and a series of oligonucleotide primers that contain the randomized sequence encoding the polypeptide library flanked by the SfiI and NotI sites and containing part of the signal peptide is used to amplify the ~250 bp region. To reduce the frequency of termination signals in the random part of the oligonucleotides, the Wobble positions of the codons are restricted to G and T residues. This restriction is designed to exclude two of the three stop codons while maintaining the inclusion of all possible amino acid residues. The amplified product is digested with KpnI and NotI and cloned into the KpnI/NotI sites of the RCASBP(A)AP display vector, a plasmid containing an infectious molecular clone of ALV(A). The plasmid library is transformed into electrocompetent DH5a bacterial host cells. The scale of ligation and transformation is sufficient to ensure that the library diversity is more than $10^7$ independent clones in each library. Successful PCR randomization of the sequences encoding the polypeptide extensions is confirmed by DNA sequencing of at least 50 independent clones from the library.

The virus library is produced by transfecting the plasmid library into multiple large flasks of chicken DF-1 cells using calcium phosphate precipitation. To characterize the virus library, genomic RNA is purified from pelleted virus particles. Once purified, the region encoding the randomized polypeptide sequence is amplified by reverse transcription (RT)-PCR, and the resulting amplification products are cloned into a TA cloning vector for sequencing. The nucleotide sequence, size, and diversity of at least 50 cloned PCR products is determined. A statistical analysis is performed to compare the observed frequency of the different amino acid residues at each randomized position in the polypeptide with the expected frequency as described elsewhere (Buchholz et al., *Nat. Biotech.*, 16:951–954 (1998)). The scale of the virus production should be enough to generate a library with a diversity of greater than $10^7$. Virus library titers of ~$10^6$ ifu/mL before virus concentration are obtainable since the viruses with chimeric surface glycoproteins replicated to ~$10^6$ ifu/mL as demonstrated herein. Virus titers can be increased by concentrating virus using centrifugation.

Example 3

Optimizing a polypeptide Display Library Selection Protocol

The following techniques are used to select and identify ALV surface polypeptide chimeras that bind to specific ligands on target polypeptides or cells from a large and diverse ALV polypeptide display library. These techniques are designed to select and identify ALV surface polypeptide chimeras through multiple rounds of selection/amplification of the viral polypeptide chimeras that actually bind a target ligand over those that bind non-specifically (i.e., background).

Targets (e.g., proteins or cells) are incubated in vitro with virions displaying an epitope under conditions that optimize specific binding of the displayed epitope to the target. Unbound virus is removed by extensive washing, and the remaining bound virus is amplified by adding DF-1 cells to allow virus infection and growth. The amplified virus pool is then subjected to additional rounds of selection (e.g., incubated in vitro with the original targets) to further define the virus pool containing epitopes that specifically bind the target. After multiple rounds of selection, a population of virions displaying N-terminal polypeptide extensions that specifically interact with the desired target is obtained.

The number of rounds of selection/amplification necessary to identify a polypeptide is determined using different concentrations of the FLAG®-displaying ALV (e.g., virions made from construct 2 described in Example 1) seeded into stocks of wild-type ALV. For example, 1, 2, 5, or 10 ifu of FLAG®-displaying ALV are added to 106 ifu of wild-type ALV to generate virus mixtures. To aid in monitoring the different viruses, the FLAG®-displaying ALV is designed to encode AP polypeptide, and the wild-type ALV is designed to encode a green fluorescent protein (GFP). The virus mixtures are incubated with anti-FLAG® monoclonal antibodies immobilized on culture dishes to bind virus containing the FLAG® epitope, and multiple rounds of amplification are performed. Duplicate aliquots of the virus mixtures are also titered to determine the actual FLAG®-displaying ALV ifu added. The distribution of epitopes in the virus pool after each round of selection is determined by extracting genomic RNA from the virus pool, amplifying the region containing the displayed epitope coding sequence by RT-PCR, cloning the amplified products into TA cloning vectors, and determining the nucleotide sequence of at least 50 clones. The number of rounds necessary to select FLAG®-displaying ALV from within the virus mixtures is used as a starting point for identifying specific interactions between displayed epitopes and any desired target.

Theoretically, every possible 6-residue polypeptide should be represented in the randomized $X_{10}$ ALV polypeptide display library when the diversity of the library approaches $10^7$. Thus, the library should contain the FLAG® epitope, DYKDDDDK (SEQ ID NO:7), or at least six to seven amino acid residues of the FLAG® epitope, which could bind to the anti-FLAG® antibody. To assess the quality of the $X_{10}$ library and to conduct an additional test of the selection/amplification protocol, the anti-FLAG® monoclonal antibody immobilized on culture plates is used as the target polypeptide for selection of the ALV-$X_{10}$ library. Multiple rounds of selection/amplification are performed, and the distribution of displayed polypeptides present in the virus pool after each round is characterized as described above. This technique provides a test of the selection/amplification protocol. In addition, if an ALV containing the FLAG® epitope within the randomized region is selected, this indicates that the quality of the polypeptide library approaches or is greater than the theoretical calculations.

Example 4

Identifying Amino Acid Sequences that Interact with Human Cancer Cell Targets The ALV polypeptide display technology described herein is useful to study any cancer related polypeptide or cell. In this example, human breast cancer is studied. ALV polypeptide display libraries are used to identify novel binding ligands associated with human breast cancer in two different in vitro selection formats: (1) purified polypeptide immobilized on a solid support and (2) cells grown in culture.

To obtain polypeptides that specifically bind purified MUC1 extracellular domain, a MUC1-GST fusion protein, consisting of five MUC1 extracellular tandem repeats (20 amino acid residues each) fused to the GST epitope for purification is immobilized on culture dishes. The three ALV polypeptide display libraries can be used. The tandem repeat region of MUC1 has only one known interaction domain, ICAM-1. It is known that MUC1 is overexpressed and aberrantly glycosylated in most breast carcinomas. The differences in glycosylation possibly provide unique epitopes on normal and aberrant MUC1 that could be identified with the polypeptide libraries. These experiments are designed to identify other polypeptide interaction domains and possibly identify polypeptide candidates by searching amino acid databases with the obtained binding polypeptide sequences. In this example, the selection/amplification protocol described in Example 2 is used. The polypeptide distribution in the virus pool is determined after each round of selection. Putative specific polypeptides that bind MUC 1 are engineered back into the ALV(A) molecular clone (inserted between the SfiI and NotI sites), and the binding specificity and affinity of the individual viruses to MUC1 determined. Also, if appropriate, glycosylation sites are mutated to determine the relative contribution of glycosylation to binding affinity.

To obtain polypeptides that specifically bind breast carcinoma cells expressing high levels of aberrant MUC1, a human breast carcinoma cell line that express high levels of MUC1 (e.g., MCF-7 and T47D) and a cell line with a low level or negative for MUC1 (e.g., MDA-MB-231 and MDA-MB-435) are used to select polypeptides that can differentiate between the two cell types. The three ALV polypeptide display libraries can be used. The polypeptide distribution in the virus pool is determined after each round of selection. After characterizing the putative specific polypeptides, some of the polypeptides selected that specifically bind MUC1 are compared to polypeptides selected using the purified MUC1 polypeptide for differences in binding purified MUC1 and aberrant MUC1 on the carcinoma cell surface.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A nucleic acid molecule comprising a first nucleic acid sequence, wherein said first nucleic acid sequence encodes a first polypeptide comprising an avian leukosis virus surface glycoprotein amino acid sequence and a first amino acid sequence, wherein said first amino acid sequence is heterologous to naturally occurring avian leukosis virus amino acid sequences, and wherein said first amino acid sequence is attached to the amino-terminal portion of said avian leukosis virus surface glycoprotein amino acid sequence, wherein said avian leukosis virus surface glycoprotein amino acid sequence comprises the sequence set forth in SEQ ID NO:1.

* * * * *